United States Patent [19]
Sackner et al.

[11] Patent Number: 6,015,388
[45] Date of Patent: Jan. 18, 2000

[54] METHOD FOR ANALYZING BREATH WAVEFORMS AS TO THEIR NEUROMUSCULAR RESPIRATORY IMPLICATIONS

[75] Inventors: Marvin A. Sackner, Miami Beach; D. Michael Inman, Miami, both of Fla.

[73] Assignee: Nims, Inc., Miami Beach, Fla.

[21] Appl. No.: 09/040,144

[22] Filed: Mar. 17, 1998

Related U.S. Application Data

[60] Provisional application No. 60/039,326, Mar. 17, 1997.

[51] Int. Cl.$^7$ ..................................................... A61N 5/00

[52] U.S. Cl. ............................................. 600/529; 600/534

[58] Field of Search .................................... 600/529–538; 128/897–898

[56] References Cited

U.S. PATENT DOCUMENTS

| | | | |
|---|---|---|---|
| 4,308,872 | 1/1982 | Watson et al. | 128/725 |
| 4,834,109 | 5/1989 | Watson | 128/721 |
| 5,348,008 | 9/1994 | Bornn et al. | 128/642 |
| 5,520,192 | 5/1996 | Kitney et al. | 128/716 |
| 5,535,738 | 7/1996 | Estes et al. | 128/204.23 |
| 5,617,847 | 4/1997 | Howe | 128/204.23 |
| 5,720,709 | 2/1998 | Schnall | 600/538 |

OTHER PUBLICATIONS

Chadha TS, Lang E, Birch S, Sackner MA. Respiratory drive in nonsmokers and smokers assessed by passive tilt and mouth occlusion pressure. Response to rebreathing carbon dioxide. Chest 1985;87:6–10.

DiFiore JM, Martin RJ, Dreshaj I, Adams JA, Sackner MA. Peak acceleration of respiratory waveforms at onset of inspiration, a new nonivasive measure of respiratory drive. Pediatr.Res. 1997;41 (Part 2):251A(Abstract).

Lopata M, Evanich MJ, Lourenco RV. Quantification of diaphragmatic EMG response to $CO_2$ rebreathing in humans. J.Appl.Physiol. 1977;43:262–270.

Milic–Emili J, Grassino AE, Whitelaw WA. Measurement and Testing of Respiratory Drive. In: Hornbein TF, ed. Regulation of Breathing, New York: Marel Dekker, 1981:675–743.

*Primary Examiner*—Cary O'Connor
*Assistant Examiner*—Michael Astorino
*Attorney, Agent, or Firm*—Cohen, Pontani, Lieberman & Pavane

[57] ABSTRACT

A method for measuring respiratory drive includes determining a peak inspiratory flow and a peak inspiratory acceleration from a breath waveform derived from rib cage motion and abdominal motion using a plethysmograph or other external respiratory measuring device. The respiratory drive is ascertainable even during complete blockage of the respiratory system. The peak inspiratory drive derived using the inventive method is used to initiate inspiration in a mechanical ventilator and for determining an index describing a shape of the waveform for controlling a continuous positive air pressure (CPAP) device.

37 Claims, 16 Drawing Sheets

METHOD FOR ANALYZING BREATH WAVEFORMS AS TO THEIR NEUROMUSCULAR RESPIRATORY IMPLICATIONS

RELATED APPLICATIONS

This application claims priority from provisional application No. 60/039,326, filed on Mar. 17, 1997 the entire disclosure of which is expressly incorporated herein by reference.

BACKGROUND OF THE INVENTION

1. Field of the Invention

The present invention relates to a method for measuring respiratory drive from breath waveforms using peak inspiratory flow and acceleration. The present invention also relates to an inductive plethysmographic system with a rapid sampling rate and a reduced signal to noise ratio that diminishes variability in the new measures of respiratory drive among other applications. The present invention further relates to the use of an inductive plethysmographic system as a trigger for initiating mechanical ventilator inflation and the use of the two measures of respiratory drive along with breath waveform shape to control the level of continuous positive airway pressure (CPAP) to eliminate obstructive sleep apneas and increased upper airway resistance during sleep.

2. Description of the Related Art

Breath waveforms and patterns of breathing are shaped and modulated, respectively, by neural discharges to the respiratory muscles from the respiratory center in the brain and the response to those impulses by respiratory muscles acting upon mechanical components of the respiratory system. Devices that provide analog waveforms of breathing, such as spirometers or pneumotachographs, have been utilized to provide information on respiratory drive that originates from the brain and the mechanical factors affecting configuration of the breath waveforms.

The most direct representation of respiratory center activity or "drive" to the respiratory muscles is the diaphragmatic electromyogram (Edi). The rate of rise (mean slope) of the moving time averaged Edi (mtaEdi) gives the most consistent results as a measure of drive, as is reflected by the highest correlation coefficients from plots against ventilation during $CO_2$ rebreathing which is a procedure that stimulates the respiratory center. However, measuring of the Edi involves the technically difficult and uncomfortable placement of an electrode catheter within the esophagus of a patient followed by blind trial and error movements of the catheter upward and downward until a point is reached at which maximum electromyogram activity synchronous with inspiration is identified. This measure has a high failure rate due to inability to locate a site with acceptable diaphragmatic electromyogram activity.

Because of technical and invasive shortcomings of the above-described esophageal electrode procedure for collecting moving time average Edi (mtaEdi), less invasive, indirect methods for estimation of respiratory drive have been tested. These alternate methods include determination of the mechanical analog of mtaEdi from the breath waveform using mean inspiratory flow (Vt/Ti) and the mouth occlusion pressure (P0.1).

In normal circumstances, increased respiratory drive causes an increase in ventilation manifested by increased respiratory rate and tidal volume. However, increased respiratory drive may fail to increase ventilation when the mechanical properties of the respiratory system are impaired, such as when there is a high-grade respiratory obstruction. In extreme cases, as typified by obstructive apnea in which the respiratory system is fully blocked, respiratory efforts manifested by paradoxical movements of the rib cage and abdomen indicate that neural discharges from the respiratory center to the respiratory muscles take place. Because of obstructions, however, no air flows in the respiratory system. In this case, the analog breath waveforms from devices that measure breathing patterns at the airway by displacement of volume or flow, such as spirometers or pneumotachographs, respectively, do not detect the presence of respiration or drive. The waveforms from these devices are flat lines. Thus, the use of measurement of Vt/Ti as a measure of drive has limited applications in clinical practice.

Mouth occlusion pressure (i.e. the pressure developed 100 ms after an unanticipated inspiratory occlusion of the airway) has also been advocated as a robust test of respiratory drive. This process detects drive during complete airway obstruction but has a number of shortcomings. It is affected by the lung volume in which occlusion is carried out so that comparisons in a given trial can only be made if lung volume is held constant. In addition, P0.1 underestimates pressure in a nonlinear way because there are pressure losses due to the is parallel compliance of the neck and oropharynx in the respiratory system; this problem can be minimized by using esophageal rather than mouth pressure but this then makes the test invasive and less clinically acceptable. Moreover, pressure measurements from both these sites have inherent inaccuracies due to difficulties in discerning the start of inspiration from the pressure waveforms.

Studies that have measured P0.1 simultaneously in the mouth and esophagus in Chronic Obstructive Pulmonary Disease (COPD) patients during $CO_2$ rebreathing to ascertain whether either of these measurements reflects central respiratory drive found considerable variability between the pressure measured at the mouth (Pm) and the pressure measured at the esophagus (Pes) in $CO_2$ rebreathing as well as in the time difference between the two. There is significant difficulty in defining the onset of inspiration from Pes and Pm because often they lack a distinct onset of inspiration. Also, in the presence of intrinsic Positive End Expiratory Pressure (PEEP), as may occur in COPD patients, the neural onset of inspiration may differ from the mechanical onset. Recording of the external electromyogram signal may help to clarify the neural onset of inspiration, but electromyogram electrodes only record from the underlying muscle groups, and different muscle groups may be activated at different times again obscuring the time of inspiratory onset. The problem of determining the true onset of inspiratory muscle activity. from pressure data, and the likelihood that breaths are taken from different lung volumes, make it unlikely that either Pes0.1 or Pm0.1 actually represents drive in COPD.

Despite its limitations, P0.1 as a measure of drive has provided insight into the mechanism of the sensation of uncomfortable breathlessness for a given exercise activity, also known as dyspnea, which is a prominent symptom of cardiopulmonary disorders. It has been postulated that "length-tension inappropriateness" might be the cause of such breathlessness. If the length attained in the respiratory muscles were inappropriate for the tension produced relative to the patient's previous experience, the sensation of breathlessness ensues. In other words, for the amount of tension developed in the inspiratory muscles the expansion of the chest is less than expected; this statement was later modified to include "mechanical inappropriateness" such as phasic distortions of the respiratory system as other factors that might contribute to dyspnea. In clinically testing this assertion, an analogy was drawn between ". . . the amount of tension developed in the respiratory muscles" to P0.1 and between ". . . expansion of the chest" to ventilation. It was found that the ratio of ventilation to P0.1 at rest was significantly less in breathless as compared to non-breathless resting COPD patients: 3.7 vs 6.3 (p<0.01). Breathlessness was not related to the level of arterial blood gases to oxygen consumption, nor minute ventilation and respiratory rate.

In a follow-up study, the relation of respiratory drive as measured by the ratio of P0.1/Ventilation in 84 seated, resting, healthy subjects and 79 patients with either COPD (n=63) or restrictive lung disease (n=16) was analyzed. It was confirmed that resting drive as measured by P0.1 was greater in patients with lung disease than normal subjects. However, because of large intra- and interindividual variability of P0.1, there was wide overlap between the values for normal subjects and patients. Since minute ventilation is a direct consequence of respiratory drive, in each individual there was a linear relation between ventilation and P0.1. Therefore, P0.1 may be considered the input and ventilation the output of the respiratory pump. Any perturbation in mechanics of the respiratory pump, i.e. lungs and/or chest bellows, alters this relationship. The ratio of ventilation/P0.1 can be expected to provide information not only on the level of resting drive but on the state of respiratory mechanics and appropriateness or inappropriateness of drive. The study found that the ratio was unaltered by age or sex in normal subjects and sharply demarcated those with normal pulmonary function from patients with lung disease. In 99% of normal subjects, Ventilation/P0.1 was < 8 whereas in only one of 79 lung. disease patients was the value < 7.9. The authors of the study cautioned that measurement of P0.1 and ventilation be made at the same recording session because errors could arise if the measurements were separated temporarily owing to moment to moment variations in these parameters.

The increased respiratory drive and reduced efficiency of ventilation appear to be related to the flattened diaphragmatic muscle that becomes an ineffective force generator in COPD patients, a hallmark of the disease. It is known that patients with severe COPD have an increased neural drive to the intercostal and accessory muscles of respiration and greater inspiratory expansion of the rib cage than do healthy subjects. They also have reduced outward expansion or paradoxical inward displacement of the ventral abdominal wall during inspiration, meaning that diaphragmatic excursions are reduced. Discharge diaphragmatic electromyographic frequencies from diaphragmatic motor units revealed that these patients also had increased neural is drive to the diaphragm. Consequently, the reduced inspiratory expansion of the abdomen in severe COPD results from mechanical limitation of diaphragmatic contractions alone. The phenomenon in COPD patients can be simulated in normal subjects by allowing them to breathe against a pressure load, i.e. PEEP (Positive End Expiratory Pressure) of 5 to 10 cm $H_2O$ during expiration. This causes the diaphragm to descend from its normal position at end-expiratory level (EELV) and to have a flattened shape as in patients with COPD as detected by an elevated EELV.

The sensory experience of breathlessness during exercise between normal subjects and COPD patients was compared. Breathlessness was qualitatively different between exercising normal subjects and COPD patients. Regression analysis revealed that the ratio of esophageal (pleural) pressure/maximum voluntary pressure (drive measure) to tidal volume/predicted vital capacity (ventilation measure) was the strongest correlate of a standardized Borg scale of subjective breathlessness. The latter also strongly correlated with the ratio of dynamic end expiratory lung volume level to total lung capacity. The authors of this study concluded that the qualitatively discrete respiratory sensations of exertion inspiratory difficulty peculiar to COPD patients may have their origins in dynamic pulmonary hyperinflation and the resultant disparity between respiratory effort and ventilatory output.

It has also been found that respiratory symptoms and degree of airway obstruction measured with spirometry correlated poorly in adult asthmatics with moderate to severe asthma. The authors stated that the results support the recommendation that airway obstruction should be measured objectively when assessing adult patients with bronchial asthma. However, an opposite conclusion can be drawn from the study. At both rest and exercise, there is evidence that a dynamic hyperinflation of the lung correlates well with symptoms. This causes elevation of the respiratory drive to ventilation ratio (or decrease in the ventilation to respiratory drive ratio), which is compatible with the above mentioned length-tension inappropriateness theory of breathlessness.

As indicated in the preceding discussion, there are major problems with current techniques for measuring respiratory drive and ventilation. For clinical relevance, the method should ideally utilize non-invasive technology, have the capability for discrete or continuous monitoring, and analyze breath waveforms with a simple algorithm to obtain drive and ventilation simultaneously on a breath by breath or one minute average. Moving time average diaphragmatic electromyogram (mtaEdi), the "gold standard" for respiratory drive, requires insertion of an esophageal catheter, an invasive procedure reserved for research applications that cannot have widespread clinical use. Moreover, another device is needed to collect ventilation. P0.1 estimations cannot be used for continuous measurements and are problematic in terms of accuracy because of the difficulty in choosing the exact onset of inspiration from the pressure waveform, particularly in COPD patients; furthermore, a separate technology is still required for measurement of ventilation. Mean inspiratory flow (Vt/Ti) fails to track respiratory drive when the respiratory system is subjected to high resistive loading.

The standard measure of breathing pattern that measures respiratory drive, mean inspiratory flow (Vt/Ti), does not reflect drive in the presence of high grade resistive loading or during complete obstruction of the airway as in obstructive sleep apneas. Occlusion pressure, i.e. P0.1, measures drive during obstructed breathing but requires a pressure sensor at the airway proximal to the site of obstruction. This system can be used in the laboratory for discrete measurements but cannot be utilized well in sleeping or critically ill patients where continuous data is preferred. The technology has questionable accuracy in patients with COPD. Diaphragmatic electromyographic measurements of drive require insertion of an esophageal catheter and noise-free data are technically difficult to obtain. The measure is impractical for long term monitoring. Therefore, it would be desirable to have a parameter of respiratory drive that can provide noninvasive, continuous measurements during high-grade resistive and elastic loading of the respiratory system.

A non-invasive technology that can measure drive and ventilation by current methods from breath waveforms is the respiratory inductive plethysmograph. It measures breath by breath ventilation from the results of multiplication of the tidal volume by rate and it computes respiratory drive by dividing tidal volume by inspiratory time to provide the mean inspiratory flow parameter (Vt/Ti). Unfortunately, as mentioned above, Vt/Ti is a not a good indicator of drive in high grade respiratory loading situations, as may for example occur with severe bronchospasm or obstructive hypopneas, and fails to track drive at all in obstructive apneas since Vt has a value of zero during mechanical respiratory efforts.

In recent years, attention has been directed toward methods for triggering initiation of inspiratory inflations by mechanical ventilators. For babies, the concern has related to the delay and desynchronization owing to the rapid breathing rates, intrinsic airway resistance, and transmission of the pressure trigger (PT) or flow trigger (FT) pulse from the measurement site of the trigger to the respirator. This delay that leads to asynchrony between spontaneously breathing mechanically ventilated infants and the ventilator has been associated with pneumothorax, intracranial hemorrhage, and hemodynamic instability. To minimize trigger delay in babies, trigger pulses obtained from sensors placed on the body surface, such as the Grasby capsule, (an applanation device on the abdominal wall), and the impedance pneumograph, have been utilized as alternatives to devices on the airways. In adults, the major concern dealing with triggering the effects of intrinsic PEEP and delay in initiation of the ventilator breath involves overcoming PEEP with the consequence of an increase in the work of breathing. Measurements of trigger effectiveness in terms of delay, failure to trigger, and work of breathing have been made in models and patients.

FIG. 15 illustrates the considerations in computing the delay in the presence of intrinsic PEEP; FIG. 15 is reproduced from FIG. 1 in the paper by S. Nava, N. Ambrosino, C. Bruschi, M. Confalonieri, and C. Rampulla. *Physiological Effects of Flow and Pressure Triggering During Non-Invasive Mechanical Ventilation In Patients With Chronic Obstructive Pulmonary Disease*, 52 Thorax 249–254 (1997). From top to bottom, FIG. 15 depicts flow, esophageal pressure, and airway pressure. The two solid lines identify, on the esophageal pressure trace, the inspiratory effort during pre-triggering. The initial portion of esophageal pressure, between the onset of the negative deflection and the point corresponding to the crossing of zero flow (dashed line), represents the effort to overcome intrinsic PEEP. The second portion of the esophageal pressure trace, between zero flow crossing and the point of its abrupt rise (and maximum negative airway pressure), represents the effort to open the inspiratory valve of the mechanical ventilator.

In ventilated neonates, asynchrony between mechanical and spontaneous breaths may lead to impaired ventilation and gas exchange or to barotrauma. Synchronization of spontaneous and mechanical breaths increases tidal volume of mechanical breaths, reduces blood pressure fluctuations, and improves gas exchange. To synchronize ventilator-generated breaths with an infant's spontaneous breathing pattern, beginning inspiration must be acutely detected. If the response time is too long, mechanical inspiration might last into the spontaneous expiratory phase, or may even begin during expiration, which can potentially impair ventilation and gas exchange. Flow-triggered (FT) ventilators are one means to initiate inspiratory inflation of the lungs. In a study to compare the performance of an impedance trigger (IT) system with electrodes on the chest connected to the FT system, the median response time for the FT system was 115 (79–184) msec. whereas the median response time for the IT system was 169 (98–305) msec. The longer and more variable response of the impedance system was secondary to phase lag of the impedance signal caused by "chest wall distortion." Although 13% of mechanical breaths were autotriggered with the impedance system, there were no autotriggered breaths with FT.

The response time of three neonatal commercial respirators was also measured. The Draeger Babylog 8000 used flow triggering (FT) with hot wire anaemometer and a threshold of 5 ml/s. At the maximum sensitivity setting, the ventilator triggered on a spontaneous inspiratory volume 0.3 ml above the 5 ml/s flow. The Bear Cub Enhancement module has a hot wire anaemometer that serves as a flow trigger; at its maximum sensitivity, the flow rate is 1 ml/s. The Star Synch module of the InfantStar ventilator uses a Graseby pressure capsule on the abdomen as a trigger and does not have a threshold level. Recordings for response time were digitally sampled at 1000 points/s and for reliability at 200 points/s. The response time of the Star Sych was 53 (13), of the Bear Cub 65 (15) and of the Babylog 95 (24) msec.

Patient triggered ventilation (PTV) has been questioned for infants because of large trigger pressures and long delay times. Recently, four infant ventilators with flow triggering have become available; they were tested using an infant model lung simulator. The tests indicated that PTV may not be appropriate under conditions of increased ventilatory drive and small endotracheal tube in infants; e.g., the delay time was 138 msec. using a 3 mm endotracheal tube during high ventilatory drive. Delay times for any respirator, site (airway, trachea, alveolus) and diameter endotracheal tube (3 mm, 4 mm, 5 mm) were a minimum of 60 msec. The investigators concluded that PTV may not be appropriate under conditions of increased ventilatory drive and small endotracheal tube size in infants because of unacceptable delays in triggering the mechanical ventilator.

FIG. 16 illustrates how an increased resistance to flow, as might occur in patients with resistive airways disease or narrow endotracheal tubes, produces unacceptable delays in triggering mechanical ventilators from sensors placed at the airways. The recordings shown in FIG. 16 are of anesthetized monkey breathing through high resistors. MVt (tidal volume), mRC (rib cage), and mAB (abdomen) indicate Respitrace waveforms adjusted for filter delays so that timing is amatched for all traces. The true onset of inspiration is depicted from negative deflection of esophogeal (transpulmonary pressure-Ptp) and delayed onset of inspiration from the integrated pneumotachographic waveform (IPNT) in the presence of resistive loading. In this example, the delay in the onset of inspiration from the airway sensor would have been unacceptable as a trigger of an inspiratory breath from a mechanical ventilator. However, the signal from t he abdominal compartment (AB) respiratory inductive plethysmograph (Respitrace™), since it was in phase with Ptp, would have been. Other traces in this recording are indices of thoracoabdominal coordination along with their numerical values.

For adults, data on flow triggering (FT) at 1 and 5 L/m and pressure triggering (PT) at 1 cm. $H_2O$ during pressure support ventilation (PSV) and assist/control ventilation (A/C) delivered non-invasively through a full facemask to patients with COPD recovering from an acute exacerbation has also been reported. Minute ventilation, breathing pattern, dynamic lung compliance and resistance, and changes of end expiratory lung volume were the same with the two triggering systems. Measurements dealing with the work of breathing were lower with FT than PT in both PSV and A/C modes; this was because intrinsic PEEP was reduced and the time of valve opening was sooner with FT. Flow triggering (FT) more consistently reduced breathing effort than pressure triggering (PT) when used in conjunction with PSV than with constant flow assist/control ventilation. It has been reported that significant advances in this area may have to await the development of technology that enables ventilator triggering from signals closer to the patient, such as esophageal pressure. In this regard, FIG. 16 indicates that the inspiratory onset of the abdominal compartment expansion using a Respitrace™, or any other type of device that measures cross-section area or circumference, may fulfill that need. In certain situations, the inspiratory onset of RC expansion may also serve as a suitable trigger.

Continuous positive airway pressure (CPAP), usually delivered via a nasal mask from an air source with capability for adjustment of the pressure, is utilized in the treatment of obstructive sleep apnea syndrome and the "upper airway resistance syndrome." This treatment splints the upper airway and eliminates or minimizes obstructive apneas and hypopneas, and diminishes partial upper airways obstructions (upper airway resistance syndrome). The first commercially available CPAP devices had pressure controls that could be set to a fixed value. Usually, patients with obstructive sleep apnea syndrome were studied in a sleep laboratory and pressures were adjusted by personnel to a level where apneas were eliminated or greatly reduced in frequency. The patient then utilized this set pressure in a CPAP device at his/her home setting. With recognition that a spectrum of airway obstructions exists in obstructive sleep apnea syndromes which vary throughout the night—ranging from complete obstruction, apnea, to partial obstruction as exemplified by hypopneas and the "upper airway resistance syndrome"—this treatment has been reevaluated. Even partial obstructions can cause arousals and sleep deprivation leading to daytime hypersomnolence, a hallmark of respiratory related sleep disturbances.

CPAP devices have been devised to automatically modify the level of pressure applied through analysis of the shape of the inspiratory flow waveform and detection of apneas through flow measuring devices on the inspiratory and expiratory ports of these devices. It has been known for many years that an inspiratory flow waveform has a sinusoidal shape in unobstructed breathing and is flattened or rectangularly shaped in the presence of inspiratory upper airways obstruction. The shape of the inspiratory flow pattern can be expressed as a numerical index by dividing peak inspiratory flow by mean inspiratory flow (PIF/MF). A sinusoidal shaped inspiratory flow waveform that is indicative of unobstructed breathing has a PIF/MF value of pie/2=3.14/2=1.57. A perfect rectangularly shaped, inspiratory flow waveform has a PIF/MF value of 1.0. Significant flattening from a sinusoidal shape occurs at a PIF/MF value of about 1.3 and below.

Variants of this index have been used to continuously compute the index and adjust CPAP pressures as a damped closed loop response. These devices may also incorporate a microphone as a snoring indicator and adjust the level of CPAP in response to snoring sounds. Apneas are also detected and the level of CPAP can be adjusted accordingly. Air leaks in the system or mask-face or nasal prongs-nasal interfaces are detected as a discrepancy between the inspiratory volume delivered by the CPAP device versus the value recorded at the expiratory part as a measure of quality control.

A new self-titrating CPAP device recently introduced into commerce monitors the device rather than the patient. High pressures within the tubing leading to the mask can lead to loss of volume delivered to the patient as a function of the compliance of the tubing and such volumes are not accounted for. Leaks at the mask-face interface cannot be accurately measured. If the CPAP mask or CPAP nasal prongs (used as a means to deliver CPAP to infants) slips off the face, all data from breathing are thereafter lost to monitoring and analysis. Pneumotachographs, i.e. flow measuring devices placed within the inspiratory and expiratory ports of these devices, may be inaccurate because accuracy suffers when they are put in line with high system pressures. Furthermore, such devices cannot accurately distinguish central from obstructive apneas.

OBJECTS AND SUMMARY OF THE INVENTION

It is accordingly an object of the present invention to provide a method for determining respiratory drive using the new parameters of peak inspiratory flow and acceleration from the breath waveforms of a subject.

It is another object of the invention to provide a respiratory inductive plethysmograph with a high enough sample rate to accurately determine peak inspiratory flow and acceleration.

It is a further object of the invention to provide a method for triggering initiation of a Mechanical Ventilator Inflation using the new parameters of peak inspiratory flow and acceleration.

It is yet another object of the invention to provide a method for controlling continuous positive pressure breathing devices using the new parameters of peak inspiratory flow and acceleration.

As mentioned above, the prior art indicates that the diaphragmatic electromyogram obtained with placement of an esophageal electrode catheter is currently considered the "gold standard" for assessment of respiratory drive in humans. The mean slope of moving time averaged diaphragmatic electromyogram (mtaEdi) is the most consistent parameter heretofore derived for drive as established by its increasing values during stimulation of the respiratory center drive with $CO_2$ rebreathing; it is analogous to its mechanical transformation, Vt/Ti from the breath waveform, but does not suffer from the mechanical limitation since the trough-to-peak amplitude of mtaEdi is also a good measure but slightly less consistent than the mean slope.

A search was performed in an effort to identify other potential parameters derived from mtaEdi that may indicate respiratory drive. FIGS. 1, 2 and 3 were located through a review of papers in the related literature in which respiratory drive was changed by a stimulus or state and the mtaEdi waveform was displayed with either tidal volume or flow breath waveform.

FIG. 1 is adapted from FIG. 9 of J.Orem, C. A. Anderson, *Diaphragmatic Activity During REM Sleep*, 81 J.Appl. Physiol. 751–760 (1996). That figure shows that the mean slope of mtaEDi is steeper in REM than NREM sleep and is in agreement with the results from discharge frequency of medullary I-aug neurons. Moreover the peak slope (i.e. the steepest tangent line that we have shown on the diaphragm electromyogram trace) is also steeper in REM than in NREM sleep, indicating that this measure has potential as a marker of respiratory drive. Finally, the steepest tangent line shown on the Flow trace, equivalent to peak acceleration, is also greater in REM than in NREM sleep, suggesting that peak inspiratory acceleration might be a measure of respiratory drive.

FIG. 2 is adapted from FIG. 3 of M. Gorini, M. Estenne, *Effect of Head-Up Tilt on Neural Inspiratory Drive in the Anesthetized Dog*, 85 Respir.Physiol. 83–96 (1991). Both the mean and peak slopes (shown as tangents to the steepest slope) of the Phrenic ENG (phrenic neurogram) increase when the anesthetized dog is tilted head-up. The steepest lines tangent to the inspiratory limb of the Lung Volume trace are equivalent to the peak slope of the derivative or flow trace; these also increase with head-up tilt, suggesting that peak inspiratory flow might serve as a marker of respiratory drive.

FIG. 3 is adapted from FIG. 2 of W. A. LaFramoise, D. E. Woodrum, *Elevated Diaphragm Electromyogram During Neonatal Hypoxix Ventilatory Depression*, 59. Appl.Physiol. 1040–1045 (1985). Tangent lines have been added to the original figure at the steepest slope of the Integrated Electromyogram trace (mtaEdi) and the Vt trace. Both peak and mean slopes of these two parameters increased when hypoxic gas mixtures were administered to infant monkeys. This suggests that peak inspiratory flow from pneumotachograph or respiratory inductive plethysmograph might be markers of respiratory drive.

Thus, analysis of FIGS. 1, 2 and 3 reveals that peak inspiratory flow and peak acceleration values from breath waveforms are candidates for correlation to the mean slope of mtaEdi, the "gold standard" of respiratory drive, and related Edi parameters during stimulation of the respiratory center with $CO_2$ rebreathing. Both of these parameters avoid the problems of potential inaccuracies of P0.1 and Vt/Ti. That is, the peaks in each of these parameters are easily selected by eye or with a computer program and are independent of selecting the point at which inspiration begins. Peak inspiratory flow has not been recognized as a marker of respiratory drive in the medical literature. Further, the peak acceleration of a breath waveform has not previously been described as any sort of parameter of the breathing pattern in the medical literature. It is noteworthy that peak acceleration takes place in the early part of inspiration, a point that is of particular interest in light of experiments which show that for both eucapneic (room air breathing) and $CO_2$ breathing, most neurons were recruited during the first 30% of the inspiratory breath time.

Although both peak inspiratory flow and acceleration tidal breath parameters are by themselves attractive candidates to serve as markers of respiratory drive, they still exhibit the same limitations of mean inspiratory flow (Vt/Ti), i.e. the inability to track drive in high grade or complete upper airway obstruction, obstructive hypopneas or apneas. However, the semi-quantitatively calibrated respiratory inductive plethysmograph, offers the additional capability of indirectly assessing values of tidal peak inspiratory flow and acceleration from the rib cage and abdominal compartments of the respiratory system. Obstructive apneas are diagnosed from the presence of completely paradoxical expansions of the rib cage (RC) and abdominal (AB) compartments of equal amplitude such that the sum of the two, the tidal volume, depicts a flat trace. These paradoxical expansions of RC and AB are synchronous with respiratory efforts as depicted from fluctuations of esophageal pressure. Therefore, measurements of peak inspiratory flow and acceleration on the RC and AB traces of the respiratory inductive plethysmograph should serve as accurate measures of respiratory drive.

To measure the respiratory drive from breath waveforms during tidal breathing in accordance with the present invention, the peak inspiratory flow and acceleration are derived from breath waveforms of the respiratory inductive plethysmograph to serve as indicators of drive from the respiratory center in the brain. Sensors of the plethysmograph are separately positioned over the rib cage and abdominal compartments and their values are summed to give tidal volume. Peak inspiratory flow and acceleration values are obtained from the tidal volume, rib cage and abdomen waveforms. Use of the peak inspiratory flow and acceleration parameters from the respiratory inductive plethysmograph provides noteworthy improvements over the prior art in that the technology is non-invasive, has the capability for discrete or continuous monitoring, and analyzes breath waveforms with a simple algorithm to obtain the drive parameters.

The measurement of breath by breath peak inspiratory flow and acceleration, and breath by breath ventilation as the product of respiratory rate and tidal volume of the breath as herein described, also permit simultaneous computation of the ratio of respiratory drive to ventilation on either a breath by breath or a time average basis. The ratio of peak inspiratory flow to ventilation is a dimensionless number and is not affected by errors in volume calibration of the measurement device. The ratio of peak inspiratory acceleration to ventilation yields a time value and is not subject to errors in volume calibration of the measurement device. Therefore, the ratio of drive to ventilation provides an objective measure of breathlessness.

The peak inspiratory acceleration values are measured during the early part of inspiration, nominally within a window approximately ±300 msec. near the beginning detection of initial inspiration from breath waveforms. The peak inspiratory flow and acceleration values may be obtained from any type of instrument capable of collecting solely tidal volume or airflow, such for example as, spirometers, pneumotachographs, body plethysmographs, naso-oral thermistors and naso-oral thermocouples among others. Peak inspiratory acceleration values may be obtained from instruments measuring respiration that are applied externally to the body surface such as the respiratory inductive plethysmograph, jerkin plethysmograph, linear differential transformers, magnetometers, bellows pneumograph, strain gauges, piezoelectric devices, and inductance circumferential transformers among others. Other external respiratory monitoring devices such as the impedance pneumograph and video transformation of torso movements into a waveform display currently provide estimates of only tidal volume. Peak acceleration values may be obtained from instruments such, for example, as those providing airway pressure, intrapleural pressure, transdiaphragmatic pressure, neck inductive plethysmography and breath sound measurements.

The basis for the assertion that values of peak inspiratory flow and acceleration measure respiratory drive is their good statistical correlation to parameters derived from the moving time average diaphragmatic electromyogram Edi. Measures from the latter are considered as the standard by which other methods such as the respiratory based peak inspiratory and acceleration parameters herein described, must be compared.

Measurement of peak inspiratory flow and/or acceleration from the aforementioned devices has diagnostic importance in numerous situations in which measurements of respiratory drive are required or effected, including:

To assess the integrity of the respiratory center in the brain by the breathing of CO2 and/or low O2 gas mixtures—respiratory drive normally increases with such stimulation;

To assess baseline respiratory center activity across wake and sleep states and ascertain abnormalities; normally, drive is highest in the wake state, intermediate in the Active or REM state, and lowest in Quiet or NREM state;

To assess respiratory center drive during obstructive apneas/hypopneas where tidal volume may be absent or negligible but in which peak inspiratory flow and acceleration values from the rib cage and abdominal compartments can provide a measure of respiratory drive;

To detect the presence of external expiratory resistive loading during sleep such as snoring and/or "tupper airway resistance syndrome";

To serve as a set-point for a manual or servo titration of positive airway pressure of patients with snoring and/or "upper airway resistance syndrome";

To monitor for presence of bronchoconstriction which increases drive in patients at risk such as patients with asthma, chronic obstructive pulmonary disease, cystic fibrosis, etc.;

To gauge the effect of anesthetic, sedative and analgesic agents that usually depress respiratory drive;

To categorize respiratory drive in various diseases as a measure of status;

To assess the status of drive during mechanical ventilation; if a patient is completely controlled by a mechanical ventilator, then drive will be virtually absent whereas if the patient is making efforts against the ventilator, the peak inspiratory flow and acceleration values will reflect this situation. In the former, peak inspiratory flow or acceleration would be equivalent to ventilator peak inspiratory flow or acceleration alone, whereas in the latter circumstance the values would be greater.;

To assess the status of respiratory muscles during potentially fatiguing tasks such as 1) elastic loading as in pulmonary edema or Adult and Infant Respiratory Distress Syndromes, 2) resistive loading as in asthmatic attacks, COPD, and upper airway resistance syndromes, and 3) during cardiogenic and non-cardiogenic shock states;

As an indirect means to signal hypoxemic events in newborns—respiratory drive increases;

As a means to signal retained tracheobronchial secretions since drive may increase under these circumstances;

As a means to diagnose nocturnal brochospasm during sleep;

As a means to detect respiratory center depression after administration of narcotics to depress excessively high respiratory drive;

As a means to monitor for presence of intrinsic PEEP (positive end expiratory pressure);

As a means to detect respiratory distress in workers or military personnel working in hazardous gaseous environments.

The invention also contemplates the use of a plethysmograph with a high enough sample rate to accurately determine the peak inspiratory flow and acceleration and the use of these new parameters as a trigger for initiating mechanical ventilator inflation breaths and as a control for a continuous positive pressure breathing apparatus.

The present invention also provides a rapid response inductive plethymographic system that increases the prior art signal sampling rate by a factor of four. The inventive arrangement reduces the band frequency divider from 4096 cycles to 1024 cycles, increases the oscillation period counter from 10 MHz to 40 MHz, and replaces isolation pot cores used in prior art systems with high performance toroids. The system also improves the signal-to-noise ratio by increasing the number of turns of the transducer around the body part being monitored. The signal-to-noise ratio is also improved by mounting the oscillator module directly on the transducer and hooking it to a demodulator system on the body to eliminate the heretofore present long recorder electrical cable, a major source of electrical noise. Additional electronic improvements have been made to reduce the size of the system and to accommodate additional inductive plethysmographic channels on the same card that currently allows only two channels. This new plethysmographic system advantageously improves the measurement accuracy of peak inspiratory flow and acceleration values. The rapid sampling rate permits accurate inductive plethysmography breath waveform displays of breaths during high frequency ventilation (i.e. respiratory strokes between 4 and 15 Hz).

The rapid response system also improves the accuracy for rapid triggering of the initiation of inspiratory inflation by mechanical ventilator devices, and provides enhanced timing accuracy of inductive plethysmographic measurements of ventricular volume, systolic time intervals, and carotid and internal jugular venous pulses.

The invention additionally provides a method for using a self-titrating CPAP device in which the preferred embodiment comprises a respiratory inductive plethysmograph and a CPAP device powered by a compressed air source connected by tubing to a nasal mask or nasal prongs such that the level of pressure responds to the calibrated waveforms of the respiratory inductive plethysmograph. A damped closed loop control system is utilized to adjust levels of CPAP in response to the index that describes the shape of the inspiratory and expiratory air flow waveforms obtained with respiratory inductive plethysmography. The indices used to control the CPAP device are peak inspiratory flow divided by mean inspiratory flow (PIF/MEF), and peak expiratory flow divided by mean expiratory flow (PEF/MEF). Values for these indices should be maintained within a range of approximately 1.31 to 1.85. When values fall outside of this range, more CPAP is applied; if values fall within the range, then CPAP levels are maintained or gradually reduced. PIF/MIF and PEF/MEF values can be utilized for manual override of the self-titrating CPAP device. Values of respiratory drive and ratio of drive to ventilation, as derived from peak inspiratory flow and acceleration of the respiratory inductive plethysmographic breath waveforms, can be used as a confirmatory test of the optimal CPAP level in patients with obstructive sleep apnea/hypopnea and upper airway resistance syndrome, viz. the higher the drive, the greater the CPAP level needed. Values of respiratory drive and ratio of drive to ventilation as derived from peak inspiratory flow and acceleration of the respiratory inductive plethysmographic breath waveforms can also be used to adjust CPAP level in patients with dynamic hyperinflation, viz. the higher the drive, the higher the CPAP level.

Other objects and features of the present invention will become apparent from the following detailed description considered in conjunction with the accompanying drawings. It should be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote similar elements throughout the several views.

DETAILED DESCRIPTION OF THE PREFERRED EMBODIMENTS

Figure 1:
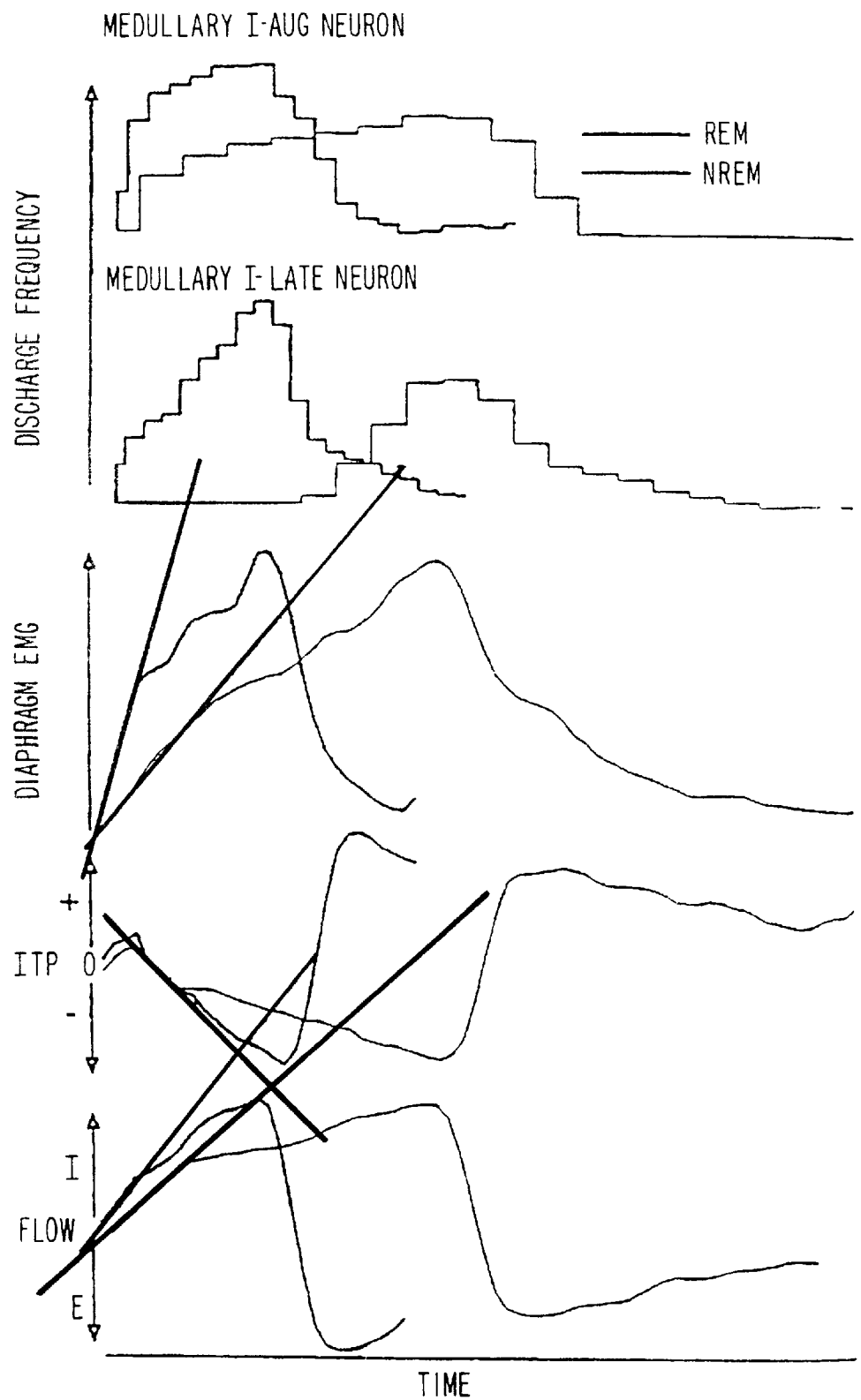
FIGS. 1–3 are graphs depicting breath waveforms.
Figure 2:
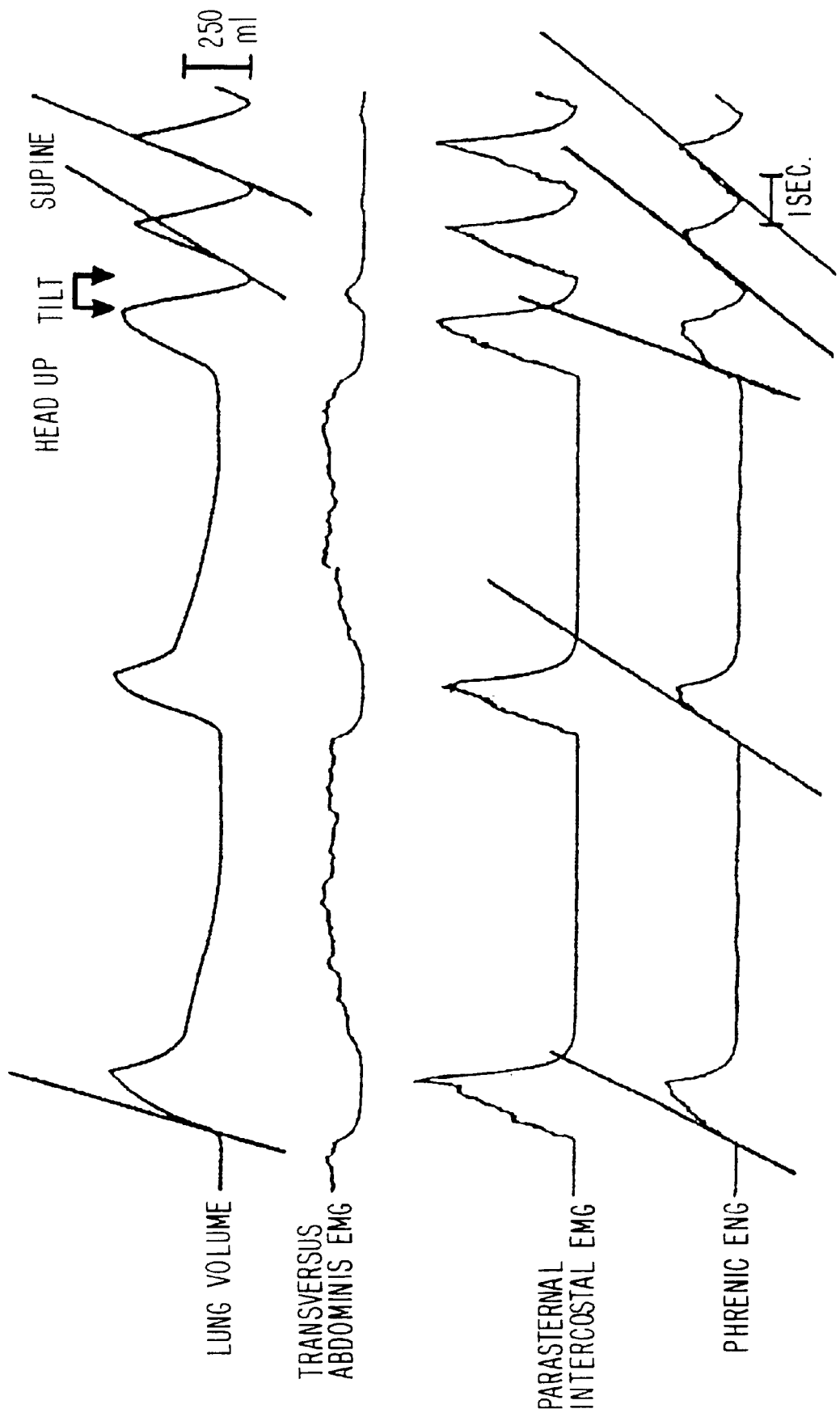
Figure 3:
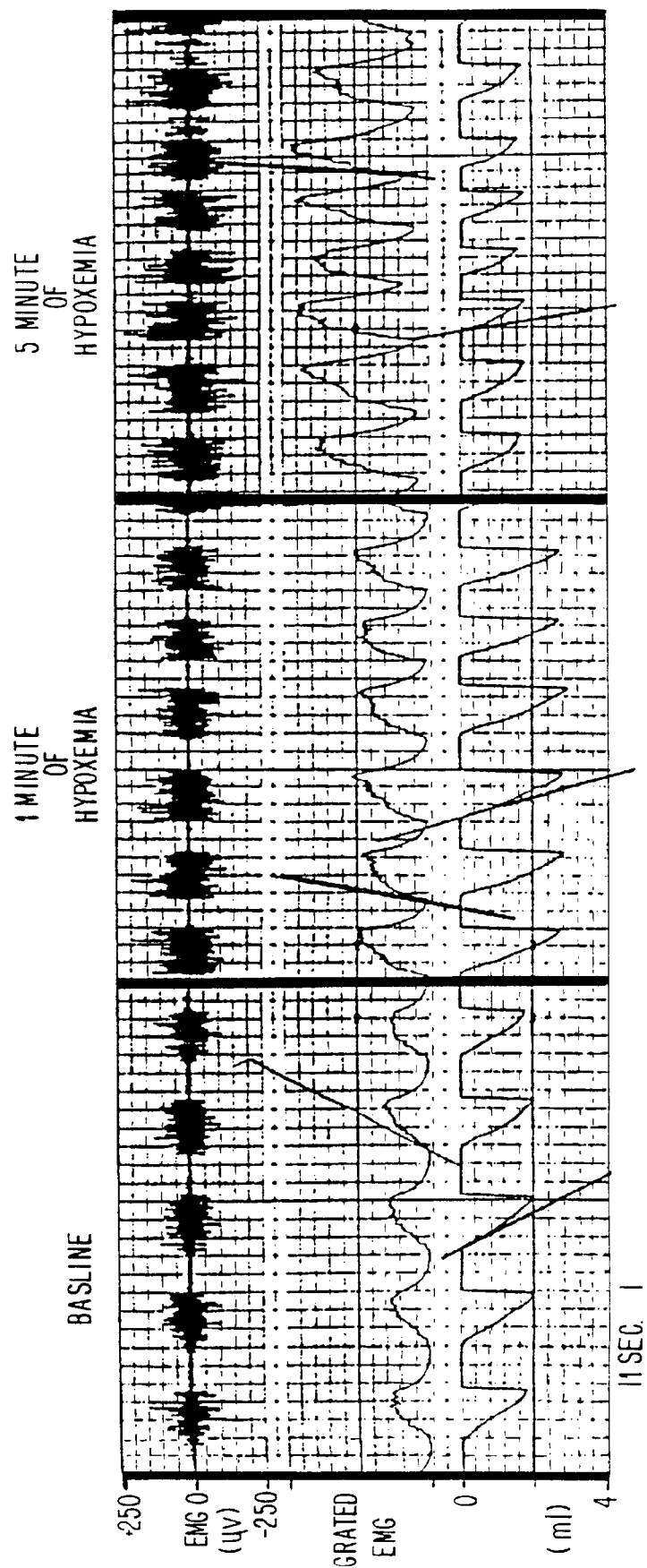

Respiratory drive comprises the complex steps in the transformation of the output of respiratory centers (i.e., inputs to the brain stem and spinal cord which affect breathing) of a subject into pulmonary ventilation.

A method for determining respiratory drive in accordance with the present invention includes use of the parameters of peak inspiratory flow and inspiratory acceleration of a breath waveform. The ratio of these parameters to ventilation is also analyzed in relation to the length-tension appropriateness. Using a respiratory inductive plethysmograph, the inventive method fulfills the above-mentioned characteristics of an ideal monitor for respiratory drive. This method advantageously uses non-invasive technology, has the capability for discrete or continuous monitoring, and analyzes breath waveforms with a simple algorithm to obtain drive and ventilation simultaneously on a breath by breath or one-minute average. The following section provides experimental evidence for validating and explaining the inventive method.

The first experiment used the inventive method to validate the feline observations that respiratory drive was higher in REM than NREM sleep; its goal was to investigate and validate these findings in sleeping, normal, preterm human infants.

We were given access to a study involving measurements with a nasal mask pneumotachograph and respiratory inductive plethysmography during $CO_2$ rebreathing in supine and prone postures in preterm infants whose state was diagnosed by behavioral criteria. We reanalyzed the data with the aid of a commercial software program, RespiEvents (Non-Invasive Monitoring Systems, Inc, Miami Beach, Fla. 33139) for computation of breath by breath peak acceleration of the respiratory inductive plethysmographic breath waveforms as well as breath by breath ventilation and Vt/Ti. The results of 62 trials in 16 babies were as follows. There were no differences between the baseline and steady-state rebreathing parameters for active (REM) and quiet (NREM) states with respect to: 1) end tidal $CO_2$, 2) ventilation, 3) pneumotachograph determined tidal volume, 4) respiratory inductive plethysmographic tidal volume, and 4) differences between pneumotachograph respiratory inductive plethysmographic determined tidal volumes.

Table 1 lists the results of this investigation. Respiratory drive as measured by peak inspiratory acceleration of Vt, RC, and AB respiratory inductive plethysmographic waveforms was significantly greater in Active than in Quiet states. This was also true for mean inspiratory flow. The rise in peak inspiratory acceleration for Vt and AB was greater with $CO_2$ rebreathing in Quiet than in Active states. This finding was not reflected by peak inspiratory acceleration of RC or Vt/Ti. Table 2 indicates that the ratio of respiratory drive (peak inspiratory acceleration) to ventilation computed on a breath by breath basis from Vt (RIP) did not differ between Active and Quiet states at baseline nor during $CO_2$ rebreathing. The rise with $CO_2$ rebreathing was greater for Quiet than Active states. These experiments found that respiratory drive is greater in Active than in Quiet states in human babies, which is consistent with the results reported on cats. However, $CO_2$ stimulation of the respiratory center causes a steeper drive response in Quiet state terms such that, at the end of the $CO_2$ challenge, respiratory drives as reflected by peak inspiratory acceleration and mean inspiratory flow between the two states did not differ. The respiratory drive- $CO_2$ response results in preterm infants is a new finding. It should be cautioned that this study alone only indirectly confirms the validity of peak inspiratory acceleration parameters as a marker of respiratory drive. For full confirmation, it was necessary to compare peak inspiratory acceleration to moving time average diaphragmatic electromyogram (mtaEdi) measures as was done in the next set of experiments.

The initial validations of moving time average diaphragmatic electromyogram (mtaEdi) to peak inspiratory acceleration and peak inspiratory flow values from breath waveforms collected by the respiratory inductive plethysmograph were carried out in anesthetized piglets. Examination of the pneumotachographic airflow waveform traces and deriving their derivatives (second derivative or acceleration since airflow is the first derivative of volume) as demonstrated by the aforedescribed analysis of FIG. 1 suggested that the respiratory center drive may be reflected from the peak inspiratory acceleration of diaphragmatic activation (PIA Edi) as derived from mta Edi. This showed that acceleration was also greater in Active than in Quiet sleep, an observation not commented upon by the original investigators. Peak acceleration occurs during the first part of inspiration and probably reflects diaphragmatic muscular recruitment.

Calibrated respiratory inductive plethysmography (RIP) provides rib cage position (RC) and abdominal position (AB) and their sum (Vt) waveforms noninvasively. We therefore tested the hypothesis that RIP derived peak inspiratory acceleration signals (PIA RC, PIA AB or PIA Vt) could be used as measures of respiratory drive by validation with mtaPaEdi during unimpeded breathing and obstructed efforts. Five newborn piglets were lightly anesthetized and allowed to breathe spontaneously through cuffed endotracheal tubes. A wire electrode wire was inserted into the diaphragm using a percutaneous, subcostal approach and RIP transducers were applied to the RC and AB compartments. Peak acceleration from RIP waveforms was measured as the highest value in a window range of ±300 msec around the mechanical onset of inspiration. The same window was used for PaEdi. Data were displayed and stored on a Respitrace PT16 recorder (Nims, Miami Beach Fla.) for subsequent analysis with RespiEvents software. Interventions included 7% $CO_2$ rebreathing and manual end-expiratory obstruction of the endotracheal tube over 2–4 efforts. For $CO_2$ rebreathing, a correlation matrix was calculated for each animal and the means (SD) are listed below; * indicates r with $p<0.05$ in all 5 piglets.

| | PIA Vt | PIA RC | PIA AB | EdiA | Ventilation | Vt/Ti |
|---|---|---|---|---|---|---|
| PaEdi | .89 (.09)* | .91 (.05)* | .62 (.32) | .93 (.03)* | .90 (.15)* | .85 (.06)* |

PIA RC tracked PaEdi better than PIA AB during $CO_2$ rebreathing. In contrast, during obstructed efforts, PIA mtaEdi and PIA AB values correlated well and both were less than preobstructed breaths though EdiA (amplitude of mtaEdi) exceeded pre-obstructed breaths, suggesting that drive is not increased during brief airway occlusions. Thus, noninvasively collected respiratory waveforms have potential as alternatives to invasive diaphragmatic recordings for the study of neonatal respiratory control.

Peak inspiratory acceleration and peak inspiratory flow are markers of respiratory drive in preterm infants in experiments where Edi was not obtained. This is supported by the good, statistically significant linear correlations to measures of drive determined from moving time average diaphragmatic electromyogram in piglets. Preliminary analysis suggested that peak inspiratory flow was a more consistent measure of drive than peak inspiratory acceleration.

A further investigation of four lightly anesthetized, intubated, spontaneously breathing piglets was added to the initial investigation described immediately above. This provided a total of nine piglets for data analysis. The experimental protocol consisted of placing an electrode wire percutaneously into the diaphragmatic muscle and calibrating the respiratory inductive plethysmograph with the QDC procedure, a natural breathing method based upon the iso-volume maneuver calibration technique. The calibration was generally carried out first in the supine posture and then a series of experiments were undertaken. Following completion of the experiments, each piglet was turned to the prone posture and the experiments repeated. Finally, each piglet was maintained in the prone posture, calibration of the respiratory inductive plethysmograph was repeated, and the QDC procedure followed with a series of experiments. The experiments consisted of trials of 1) 7% $CO_2$ rebreathing for about four minutes with one minute baselines and recoveries, 2) breathing against 5 cm $H_2O$ PEEP valve for approximately three to four minutes with one minute baselines and recovery, and 3) manual occlusions of the endotracheal tube while the piglet made three or four obstructed efforts.

The $CO_2$ rebreathing trials lasted six minutes and consisted of baseline, test, and recovery periods. Data from these trials collected by a Respitrace PT 16 recorder (Nims, Miami Beach, Fla.) were processed with RespiEvents software. The resulting data was converted to ASCII text and imported by Statistica (StatSoft, Tulsa, Okla.) software for statistical analysis.

Data from $CO_2$ rebreathing trials was analyzed for correlation between mtaEdi and breath waveform respiratory drive parameters. Table 3 lists coefficient correlation [r] values computed from derivative and flow measures of mtaEdi and breath waveforms (respiratory inductive plethysmograph [RIP]) during $CO_2$ rebreathing. Means of one or more trials in the nine piglets are denoted in Table 3 by body posture and the posture in which calibration was carried out, e.g. sc is supine calibrated (QDC procedure for calibrating RIP in supine posture), pu is prone uncalibrated (QDC procedure for calibrating RIP from calibration in supine posture utilized), and pc is prone calibrated (QDC procedure for calibrating RIP in prone posture). The letter 'd' following the designation of posture and calibration in Table 3 signifies those trials in which raw data was edited by deleting outlying values. A mean of 202 breaths were collected for each $CO_2$ rebreathing trial; nine breaths (4.5%) were deleted because some measures within the breath had unacceptable outlying values when data for correlation coefficients was viewed in graph form in the statistical software program Statistica. MANOVA statistical analysis (part of the Statistica program) was applied to the data and revealed significant differences between raw and edited data for correlations between 1) ventilation and EdiA/Ti, 2) PIA Vt and EdiA/Ti, 3) Vt/Ti and EdiA/Ti, 4) ventilation and PIF Edi, and 5) Vt/ti and PIF Edi. For the remainder of the correlation coefficient comparisons, there was no statistical difference between the raw and edited data.

There were no statistical differences between the correlation coefficients and body posture and the calibration procedure from which the data were collected.

High correlation coefficients were found for measures derived from moving time average Edi and peak inspiratory flow of tidal volume (PIF Vt) measured from RIP, e.g. 0.70–0.80. From these results, it is therefore clear that peak inspiratory flow derived from the tidal volume waveform of the respiratory inductive plethysmogaph (Vt [RIP]) is a valid marker of respiratory drive.

Table 4 lists coefficient correlation [r] values computed from acceleration measures of mtaEdi and breath waveforms (respiratory inductive plethysmograph [RIP]) during $CO_2$ rebreathing. Means of one or more trials in the nine piglets are denoted in Table 4 by body posture and the posture in which calibration was carried out, e.g. sc is supine calibrated (QDC procedure for calibrating RIP in supine posture), pu is prone uncalibrated (QDC procedure for calibrating RIP from calibration in supine posture utilized), and pc is prone calibrated (QDC procedure for calibrating RIP in prone posture). The letter 'd' following the designation of posture and calibration in Table 4 signifies those trials in which raw data was edited by deleting outlying values. Moderately high correlation coefficients were found for measures derived from moving time average Edi and peak inspiratory acceleration of tidal volume (PIA Vt) measured from RIP, e.g. 0.45–0.56. These correlation coefficients were less than those from peak inspiratory flow. This difference might relate to the damped frequency response of the acceleration computation owing to the digital sampling rate of the respiratory inductive plethysmographic hardware, viz. 50 points/sec. Further experiments have indicated that new respiratory inductive plethysmographic hardware which samples at 200 points/sec. obviates this situation.

The results of Table 4 show that peak inspiratory acceleration derived from the breath waveforms of respiratory inductive plethysmography (Vt [RIP]) is a valid marker of respiratory drive.

Table 5 ranks the correlation coefficients obtained with flow and acceleration measures of respiratory drive from ascending to descending order during $CO_2$ rebreathing. Peak inspiratory flow of Vt (RIP) plotted against the most widely accepted physiological measure of respiratory drive, the mean slope of mtaEdi (EdiA/Ti), was greater than the correlation coefficient for peak inspiratory acceleration of Vt (RIP), e.g. 0.80 versus 0.56 though both had high statistical significance. The compartment peak inspiratory flows also correlated well to diaphragmatic measures of drive.

During $CO_2$ rebreathing, respiratory drive and ventilation increase; the mean slope of mtaEdi reflects this activity. Peak inspiratory flow computed from respiratory inductive plethysmography correlates well to changes in mean slope mtaEdi and therefore can be considered a noninvasive alternative to the diaphragmatic electromyographic measurement of drive. Peak inspiratory acceleration correlates less well to mean slope mtaEdi than peak inspiratory flow but is still significantly correlated to mean slope of diaphragmatic so as to be useful as an indicator of drive.

$CO_2$ rebreathing stimulates the respiratory center to discharge neural impulses to the respiratory muscles. If the muscles are not loaded, i.e. no resistive or elastic loads are imposed at the airway or chest-lung system as a result of disease or experiments, then drive and ventilation should have a linear relationship. Table 6 lists linear correlation coefficients for such relationships. As expected from the preceding discussion, there were high correlations between peak inspiratory flow Vt, mean slope mtaEdi and ventilation during $CO_2$ rebreathing. Less correlation, albeit still high, was found for mean inspiratory flow, peak slope mtaEdi, and peak inspiratory acceleration parameters.

Breath by breath values of peak inspiratory flow and peak inspiratory acceleration of breath waveforms correlate well to breath by breath values of ventilation during $CO_2$ rebreathing. This further substantiates the validity of these parameters as noninvasive measures of respiratory drive.

Another purpose of these experiments was to determine whether pulmonary hyperinflation would increase drive and/or the ratio of drive to ventilation. This postulate was tested because it is known that neural afferent discharges from a diaphragm that is flattened from application of PEEP stimulate the respiratory center.

After performing the initial $CO_2$ rebreathing experiments described above, six of the nine piglets in the study inspired air at atmospheric pressure through a cuffed endotracheal tube and expired against a PEEP value of 5 cm $H_2O$ for about three to four minutes. The end-expiratory lung volume as determined with a DC coupled respiratory inductive plethysmograph generally rose initially in response to the PEEP application. In most instances, shortly thereafter, end expiratory lung volume level returned to the pre-PEEP level through the remainder of the 3–4 minute PEEP trial. A total of 14 trials were obtained. In six trials, mean end expiratory lung volume increased in the PEEP period over baseline and in eight trials it did not change or fell in value. It is of interest that in five piglets with an electrode inserted into an expiratory respiratory muscle for recording the electromyogram, PEEP brought about active expiratory muscular contractions that appeared much larger than baseline.

There were no statistically significant changes in any of the respiratory drive or ratio of drive to ventilation parameters during PEEP as compared to baseline or recovery. Therefore, all 14 trials were analyzed with ANOVA statistical analysis followed by the Tukey honest significance difference test. There were no changes in any of the diaphragmatic electromyographic (mtaEdi) or breath waveform parameters of respiratory drive with PEEP application. Respiratory rate declined from 29.5 breaths/min to 23.3 breaths/min and tidal volume rose 27% from baseline to PEEP 5 cm $H_2O$. Ventilation was unchanged. There were no significant changes of diaphragnatic or respiratory measures of drive with PEEP application among baseline, PEEP and recovery periods. There were no significant changes in the ratios of diaphragmatic or respiratory measures of drive to ventilation between baseline and PEEP periods. However, there were significant falls from the PEEP trial to recovery in the ratios of Vt/Ti/Ventilation, PIF Vt/Ventilation, PIF RC/Ventilation, and PIA Vt/Ventilation.

Application of 5 cm $H_2O$ PEEP for three to four minutes in lightly anesthetized piglets did not affect diaphragmatic or respiratory measures of respiratory drive among baseline, PEEP and recovery periods. The respiratory and diaphragmatic ratios of drive to ventilation did not change with PEEP. This might be the result of respiratory center depression from anesthesia that blunts the response to pulmonary hyperinflation as also noted for P0.1 in anesthetized humans exposed to PEEP 16 cm $H_2O$. The elevation in drive to ventilation ratios when PEEP was compared to recovery occurred for both peak inspiratory flow and acceleration measures but not for any diaphragmatic parameters of drive. This suggests that the drive measures based upon breath waveforms might be more sensitive measures of drive.

Figure 4:
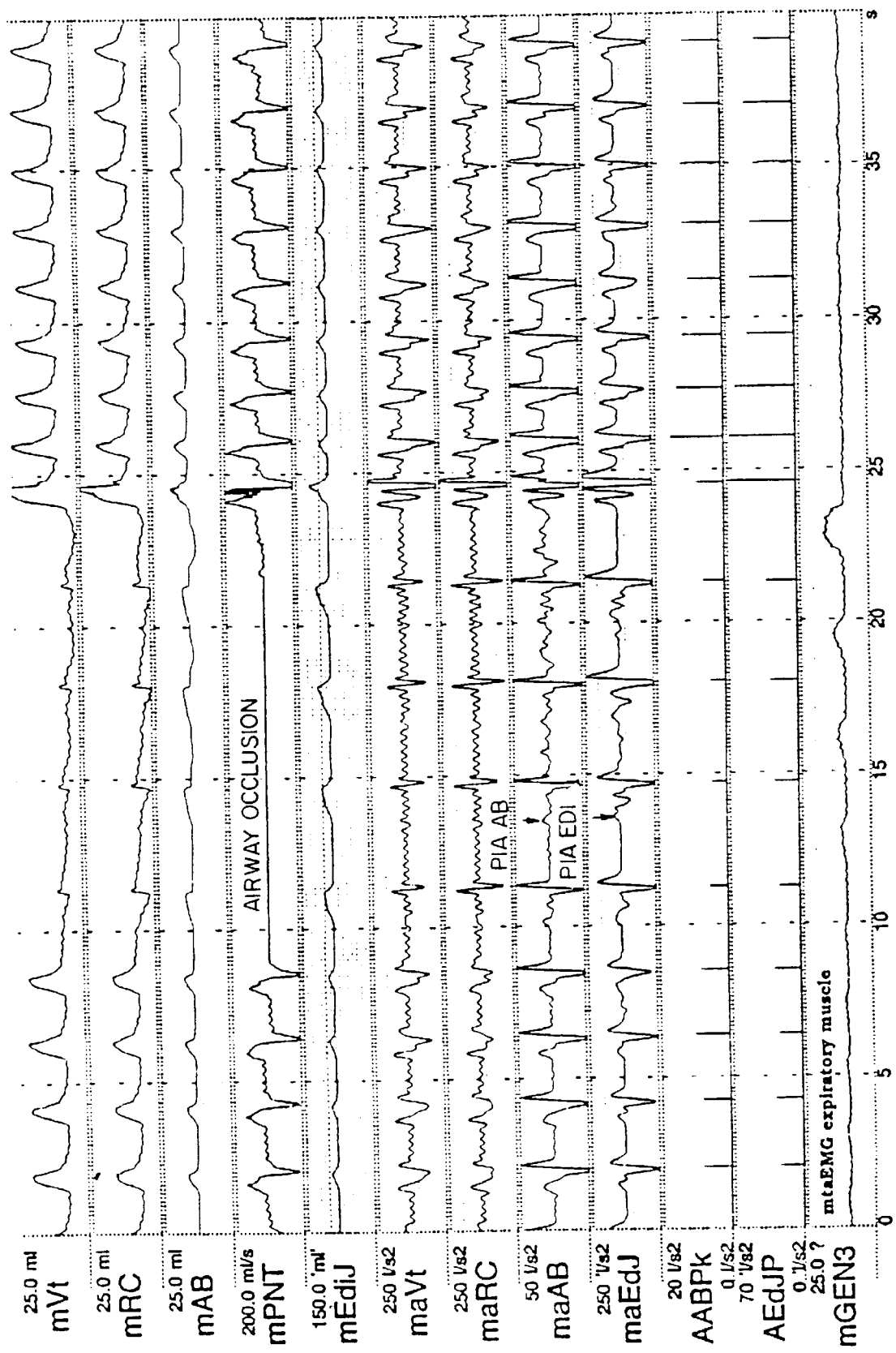
FIG. 4 is a graph plotting traces of the diaphragmatic electromyogram and peak inspiratory acceleration during airway occlusion.

Data from response to $CO_2$ rebreathing in the present series of experiments indicates that peak inspiratory flow and peak inspiratory acceleration of all components of the respiratory inductive plethysmographic technology, i.e. Vt, RC, and AB, serve as valid markers of respiratory drive. Since obstructive apneas are generally marked by diaphragmatic efforts with passive movements of the rib cage, the AB waveform can be utilized as the trace for parameters of drive. is After obtaining the initial $CO_2$ response and PEEP data as described above, the airway of each anesthetized piglet was manually occluded at end-expiration for three to four efforts. Diaphragmatic electromyographic and respiratory inductive plethysmographic measures of respiratory drive were recorded with RespiEvents software (Nims, Miami Beach Fla.). A total of 34 successful occlusions were obtained in seven of the nine piglets. FIG. 4 graphically depicts a representative tracing of manual occlusion of the airway.

FIG. 4 shows a progressive increase in amplitude of mtaEdi (mEdiJ) over the four efforts that took place during manual airway occlusion. Note 'm' denotes that the traces are 'matched' in timing for the various digital filters used on the traces. The values of PIA AB (denoted here as AABPK) fall from baseline immediately with the first occlusive effort and then 5 increase when the occlusion is terminated. The values of PIA Edi (denoted here as AEdJP) qualitatively follow the same course The mtaEdi of an expiratory muscle (mGEN3) is activated during occlusion and distorts the mAB trace with an expiratory component.

Table 7 lists the results from 34 occlusion trials which represents the means from a baseline of four to eight breaths and means from three or four efforts during manual airway occlusions. The respiratory drive parameters were computed from mtaEdi and AB RIP. With the exception of increased amplitude of moving time average diaphragmatic electromyogram of the three to four efforts during airway occlusion, there was no change of mean slope Edi, peak inspiratory flow AB, nor peak inspiratory acceleration AB. In terms of respiratory drive, the response to manual occlusion of the airway varied. In some piglets, the first effort showed decreased drive from the baseline PIA AB, whereas in others drive was maintained. Drive progressively rose over the four breaths as depicted in the representative recording (FIG. 4) or had random variations among the three or four efforts. This was not the case for PIF AB which fell with the first effort in the same way as PIA AB but did rise with further efforts, as did PIA Edi or PIA AB. This suggests that peak inspiratory acceleration may be a more consistent marker of drive during obstructive apnea than peak inspiratory flow.

In anesthetized piglets, manual occlusion of the airway produced increased amplitude of mtaEdi but no change in mean slope of diaphragmatic electromyogram, considered by many the most consistent measure of respiratory drive. Further, manual occlusion of the airway revealed increased drive from respiratory efforts according to amplitude but no change according to mean slope of diaphragmatic electromyogram. Results from the latter were similar to those found with peak inspiratory flow or acceleration of abdominal compartment of the respiratory inductive plethysmograph. Therefore, noninvasive measures from compartment breath waveforms appear to reflect respiratory drive during total airway occlusion.

Conclusions of Respiratory Drive Experiments in Anesthetized Piglets

Peak inspiratory flow or peak inspiratory acceleration during early inspiration derived from respiratory waveforms provide valid and reliable measures of respiratory drive. With normal or near normal coordinated thoracoabdominal motion, all such parameters derived from the tidal volume, rib cage or abdominal breath waveforms can be utilized. For measurements during $CO_2$ rebreathing that stimulate drive from the respiratory center, peak is inspiratory flow appears to provide slightly more consistent results than peak inspiratory acceleration. Peak inspiratory flow and acceleration values can be obtained from all instruments capable of collecting only tidal volume or airflow; such instruments include spirometers, pneumotachographs, body plethysmographs, naso-oral thermistors and naso-oral thermocouples, among others. Peak inspiratory flow and acceleration values can be obtained from instruments measuring respiration that are applied externally to the body surface such as the respiratory inductive plethysmograph as in the current study, jerkin plethysmograph, linear differential transformers, magnetometers, bellows pneumograph, strain gauges, piezoelectric devices, and inductance circumferential transformers, among others. The sensors of these devices are placed separately over the rib cage and abdominal compartments and the values summed to give tidal volume. Other external respiratory monitoring devices, such as the impedance pneumograph and video transformation of torso movements into a waveform display, currently provide estimates of only tidal volume. Peak acceleration values may also be obtained from airway pressure, intrapleural pressure, transdiaphragmatic pressure, neck inductive plethysmography and breath sound measurements.

With paradoxical motion of the rib cage (RC) and abdominal (AB) respiratory compartments, drive may be best measured from peak inspiratory flow or acceleration of the breath waveforms of the predominant compartment of breathing, viz. RC or AB rather than tidal volume which is the sum of the two, especially during high-grade resistive loading of the respiratory system, as for example severe bronchospasm in an asthmatic episode or with partial obstruction of the upper airway. In the extreme case of complete airway obstruction as in obstructive sleep apnea, peak inspiratory or acceleration values from either the RC or AB compartments estimate drive since the tidal volume trace has flat or near flat movements and its peak inspiratory or acceleration values become meaningless. The choice of RC or AB relates to which waveform has the same deflection direction of the compartment in the period of breathing prior to the obstruction, which is called the dominant or leading compartment.

The ratio of drive to ventilation as an objective measure of breathlessness or hyperinflation of the lungs may also be computed on a breath by breath basis from peak inspiratory flow or acceleration values divided by ventilation. These values were unchanged from baseline in the hyperventilation induced by $CO_2$ rebreathing since the respiratory system was not loaded in the current experiments and the drive to ventilation ratio would be expected to be appropriate. On the other hand, in the anesthetized piglets that breathed on 5 cm $H_2O$ PEEP, the drive to ventilation ratio fell significantly between the PEEP and recovery periods as would be expected when the expiratory load was eliminated. The failure to increase the ratio of drive to ventilation from baseline to PEEP in piglets might relate to the confounding effect of anesthesia that depresses drive or the failure to hyperinflate the lungs due to active expiration. In this regard, other experiments indicate that the drive (peak inspiratory flow or acceleration) to ventilation ratio increases greatly in unanesthetized sheep breathing on just 2.5 cm $H_2O$ PEEP and in normal humans on 5 to 10 cm $H_2O$ PEEP.

In a study entitled, "*Respiratory Drive and Ventilatory Response to Resistive Loads in Adult Anesthetized Monkeys*" by Newth, C. J. L., Adams, J. A., and Sackner, M. A. Children's Hospital of Los Angeles, Los Angeles, Calif. & Mt. Sinai Med Center, Miami Beach Fla., peak inspiratory flow (PIF Vt) and acceleration (PIA Vt) from respiratory inductive plethysmographic (RIP) waveforms correlate well ($r=0.80$ & $r=0.56$, respectively) to mean slope of moving time average diaphragmatic electromyogram (EdiA/Ti) in piglets rebreathing $CO_2$. In addition, PIF Vt, EdiA/Ti, and PIA Vt correlate well ($r=0.85$, $0.82$, and $0.74$, respectively) to breath by breath ventilation (Ve). RIP and pneumotachograph (PNT) drive and ventilation (Ve) parameters were measured as well as transpulmonary pressure (Ptp) in anesthetized monkeys during external inspiratory (I), expiratory (E), and combined (I+E) resistive loads [R] of 5 to 1500 cm $H_2O/l/s$ applied for 2 minutes. All animals had marked paradoxical rib cage motion at baseline (mean phase angles 100 degrees). Analysis was restricted to RIP abdominal (AB) & PNT data. The ratio of AB Pif/PNT Ve in Table 8 relates drive to ventilation as a dimensionless number; * indicates values at which parameters were significant over values at lower R's.

None of the resistances R changed the level of AB FRC. The ratio of drive to ventilation rose with both I & E, indicating failure of respiratory muscle to respond effectively to drive because of the imposed resistive load. Trace time plots revealed a delayed rise of drive with high R and a delayed fall upon switching from higher to lower R. The latter probably related to the elevated Pa $CO_2$ attendant with high R (19 Ped Pulm 167 (1995)) In anesthetized monkeys, detection of external resistive loads with noninvasive drive and drive to ventilation parameters were not as sensitive as directly measured increases of transpulmonary pressure.

The preceding study indicates that elevation in respiratory drive and the ratio of drive to ventilation occur with moderate resistive loading. Peak inspiratory acceleration appears to be more sensitive in this regard than peak inspiratory flow. No changes take place with mild resistive loads even though significant increases are found in transpulmonary pressures.

The latter directly relates to the mechanical aspects of increased load. Therefore, elevations of resistive load in the short term require that a threshold be reached before drive or the drive to ventilation ratio shows a significant increase.

Drive and the ratio of drive to ventilation parameters derived from respiratory inductive plethysmographic breath waveforms are not as sensitive for detection of increased resistive loads as transpulmonary pressure that directly measures mechanical consequences of loading. However, for detection of resistive loads, peak inspiratory acceleration appears to be more sensitive than peak inspiratory flow. If major paradoxical motion between the rib cage (C) and abdominal (AB) compartments occurs during loading, then the dominant compartment, i.e. RC or AB, must be used as the source for the respiratory drive parameter rather then tidal volume (Vt). Further, these findings suggest that elevations of drive or the ratio of drive to ventilation may be utilized in continuous monitoring situations to indicate and alarm on dangerously high resistive loads.

Another study entitled, *"Parameters of Breathing Pattern Useful for Staging State in Newborns"* (by Adams, J. A., Zabaleta, I., Sackner, M. A., Div Neonatology, Div. Pulm. Dis. Mt. Sinai Med. Center, Miami Beach, Fla.) was carried out to ascertain which parameters might be useful in differentiating among Wake, Active and Quiet states in newborns. Nine newborns, which constituted the study group, were studied on two occasions on the same day for 95 min., SD 19 min. Their activity was scored from one-minute epochs of video observations (Prechtl behavioral criteria), and from waveform recordings obtained using calibrated respiratory inductive plethysmography (RIP), pulse oximetry ($SaO_2$), and electrocardiogram with RR interval resolution to ±1 msec (Respitrace PT, RespiEvents, Nims, Miami Beach Fla.). Raw waveform traces were utilized to score state by pattern based recognition. For example, Wake=movement artifacts on breath waveform traces, Quiet=regularity of rate and Vt as well as normal thoracoabdominal coordination, and Active=irregularity of rate and Vt, paradoxical thoracoabdominal motion, and shift to a lesser contribution of rib cage motion. An empirical software algorithm, which was based upon one-minute medians and quartile ranges of the following parameters to score state was also utilized for scoring; the parameters included 1) median Vt, 2) breath to breath Vt and total breath time differences, 3) heart rate, and 4) a threshold value of phase relation during inspiration. Agreement between computer and pattern recognition was 82% SD 8%, computer and video 50% SD 15%, and pattern recognition and video 51% SD 15%. Because of poor agreement among the three methods, ANOVA statistical analysis was applied only to those epochs in which all three methods were in agreement to uncover other parameters that might distinguish among these states by the Neuman-Keuls test of significance. The following parameters of a total of 70 examined, other than those used for initial scoring, fulfilled the discriminatory criteria. Ranked in descending order of F values for significance between-groups-differences, these included: 1) percent of time RC was paradoxical to Vt in expiration, 2) phase relation of total breath, 3) phase relation of expiratory breath, 4) phase angle, 5) percent of time RC was paradoxical to Vt in inspiration, 6) ratio of abdominal peak inspiratory flow to ventilation (PIF AB/Ventilation), 7) mean inspiratory flow of Vt, and 8) quartile range of tidal peak inspiratory flow to ventilation. The first five parameters are thoracoabdominal motion indices, the next two respiratory drive parameters, and the last one a respiratory drive variability parameter. Addition or substitution of one or more of these parameters to the software algorithm should enhance its discriminatory power to distinguish among states. This modified software algorithm for staging states in newborns now appears ready for comparative trials to clinical polysomnograms.

This study indicated that utilization of respiratory drive and ratio of drive to ventilation may serve as an ancillary aid to distinguishing among sleep and wake states in newborns. Thus, drive is lowest in Quiet sleep, intermediate in Active sleep, and highest in Wake states. The ratio of drive to ventilation paralleled the drive discrimination measures alone.

It has been established that rebreathing $CO_2$ stimulates the respiratory drive such that its neural output causes increased rate and depth of breathing. Another stimulus to the respiratory drive is combined addition of inspiratory and expiratory resistors added distal to the mouthpiece of a normal adult or asthmatic patient breathing through a pneumotachograph. Resistive loading may be instituted with either bronchoconstriction induced with aerosolized methacholine or adding external resistors up to 13 cm $H_2O/l/s$ at the mouthpiece to accomplish both inspiratory and expiratory loading. Using this method on six normal adults and 11 asthmatic patients who breathed 100% oxygen during the trials, mouth occlusion pressures (P0.1) and breathing patterns were monitored. The bronchospasm induced with methacholine produced increased ventilation, rate, Vt/Ti and P0.1. Addition of external resistors reduced rate and Vt/Ti, but did not alter ventilation. End expiratory lung volume level increased to a greater extent with bronchoconstriction than external resistive loading. P0.1 increased in proportion to changes in airway resistance with both bronchostriction and external resistive loading. However, the change in P0.1 was greater with bronchoconstriction for a given change of resistance than external resistive loading. Although the subject's perception of uncomfortable breathlessness (dyspnea) increased with both types of resistive loads, at any given resistance it was higher with bronchoconstriction.

Application of positive end expiratory pressure (PEEP) to the airway produces pulmonary hyperinflation that in turn increases respiratory drive.

The purpose of the following experiments was to confirm that peak inspiratory flow and acceleration reflected the same changes in respiratory drive as in the experimental conditions reported above. Eight normal adults participated in these experiments but data are only available and described below for one representative volunteer.

Figure 5:
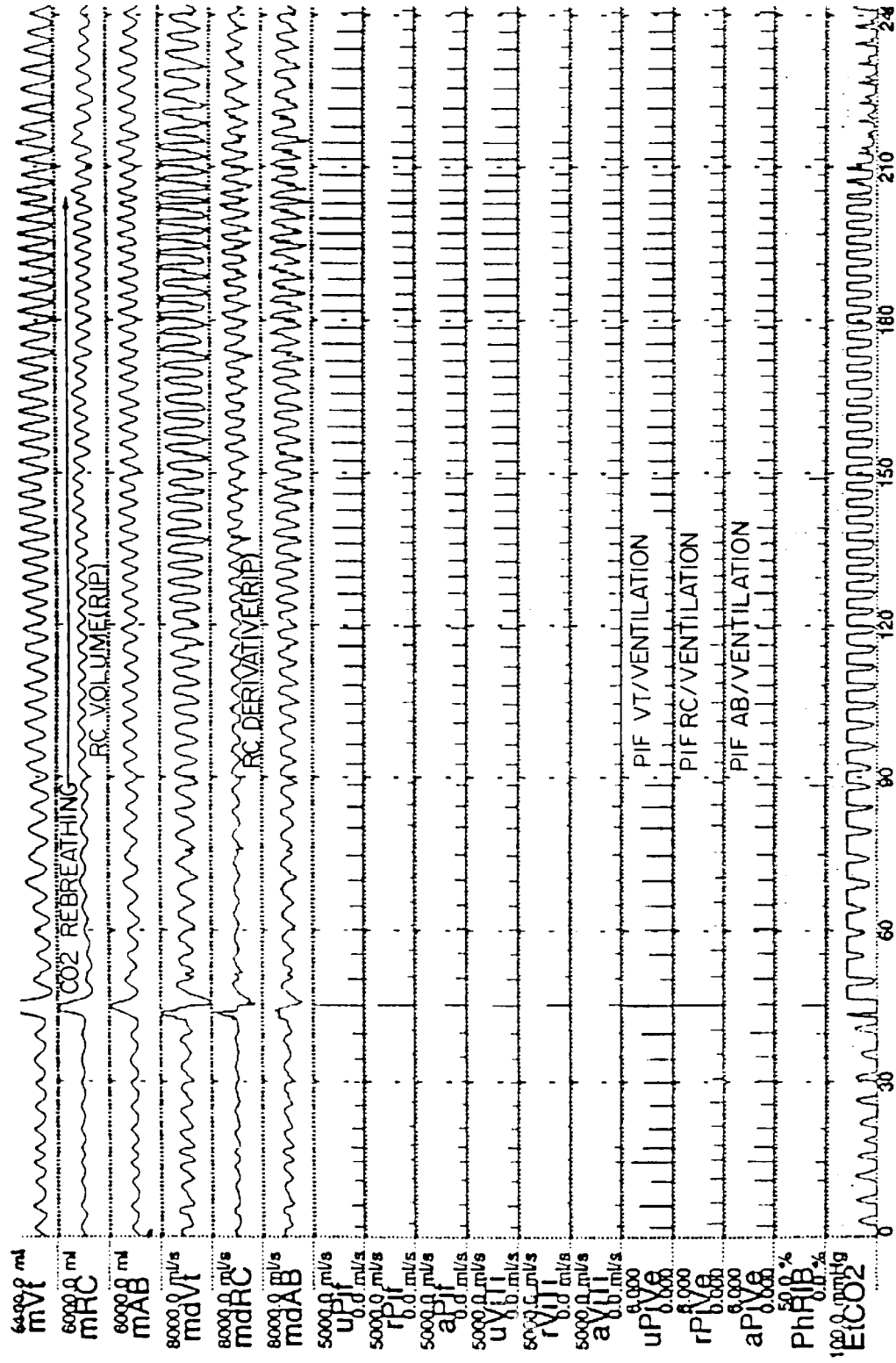
FIG. 5 is a graph showing traces of peak inspiratory flow parameters during $CO_2$ rebreathing.
Figure 6:
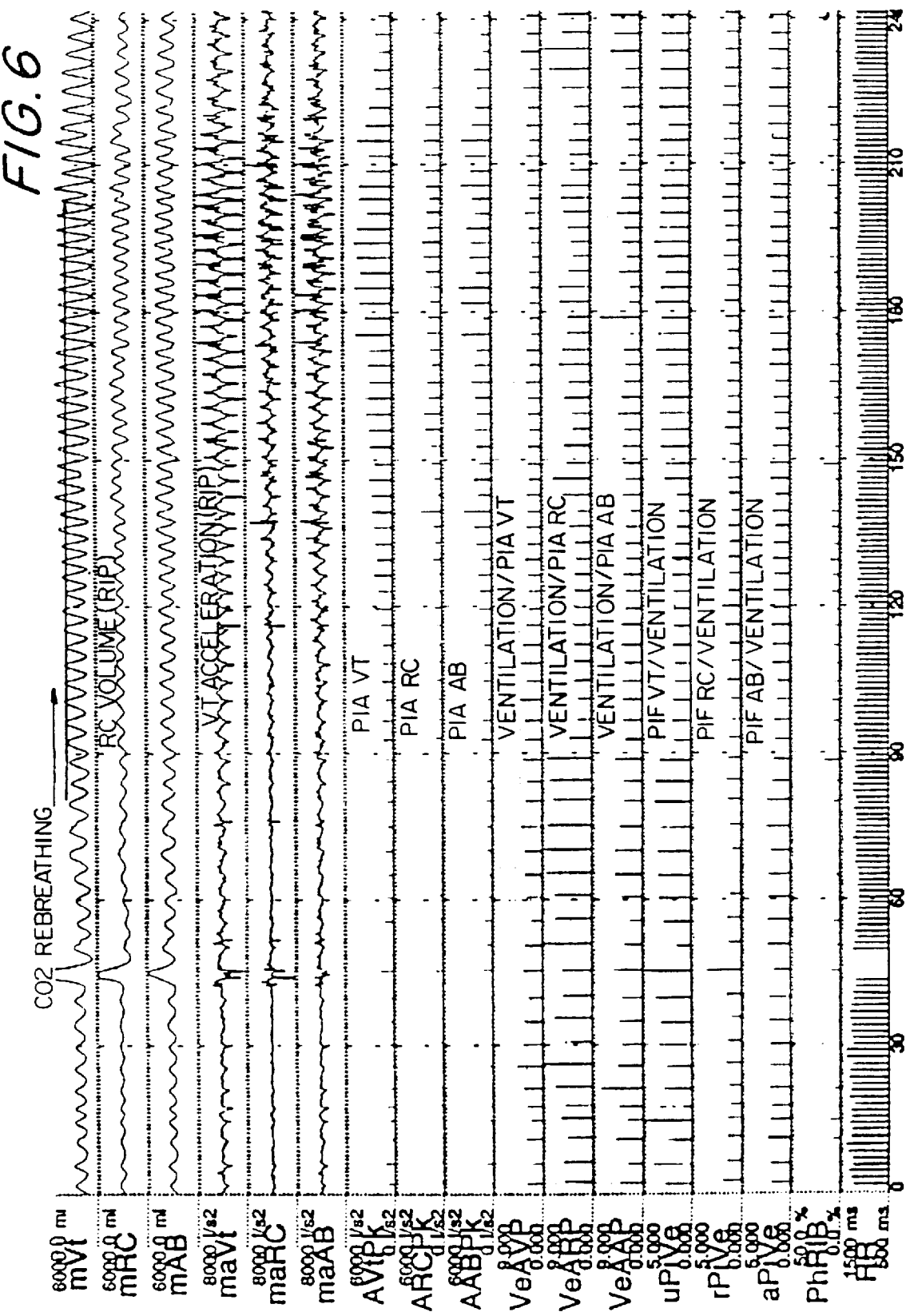
FIG. 6 is a graph plotting traces of peak inspiratory acceleration parameters during $CO_2$ rebreathing.

The study with normal adults involved rebreathing 7% $CO_2$ in an $O_2$ mixture for about three minutes. FIG. 5 depicts the response of breath waveforms to $CO_2$ rebreathing in the representative adult; it shows peak inspiratory flow parameters. FIG. 6 depicts response of breath waveforms to $CO_2$ rebreathing; it shows mostly peak inspiratory acceleration parameters.

Figure 7:
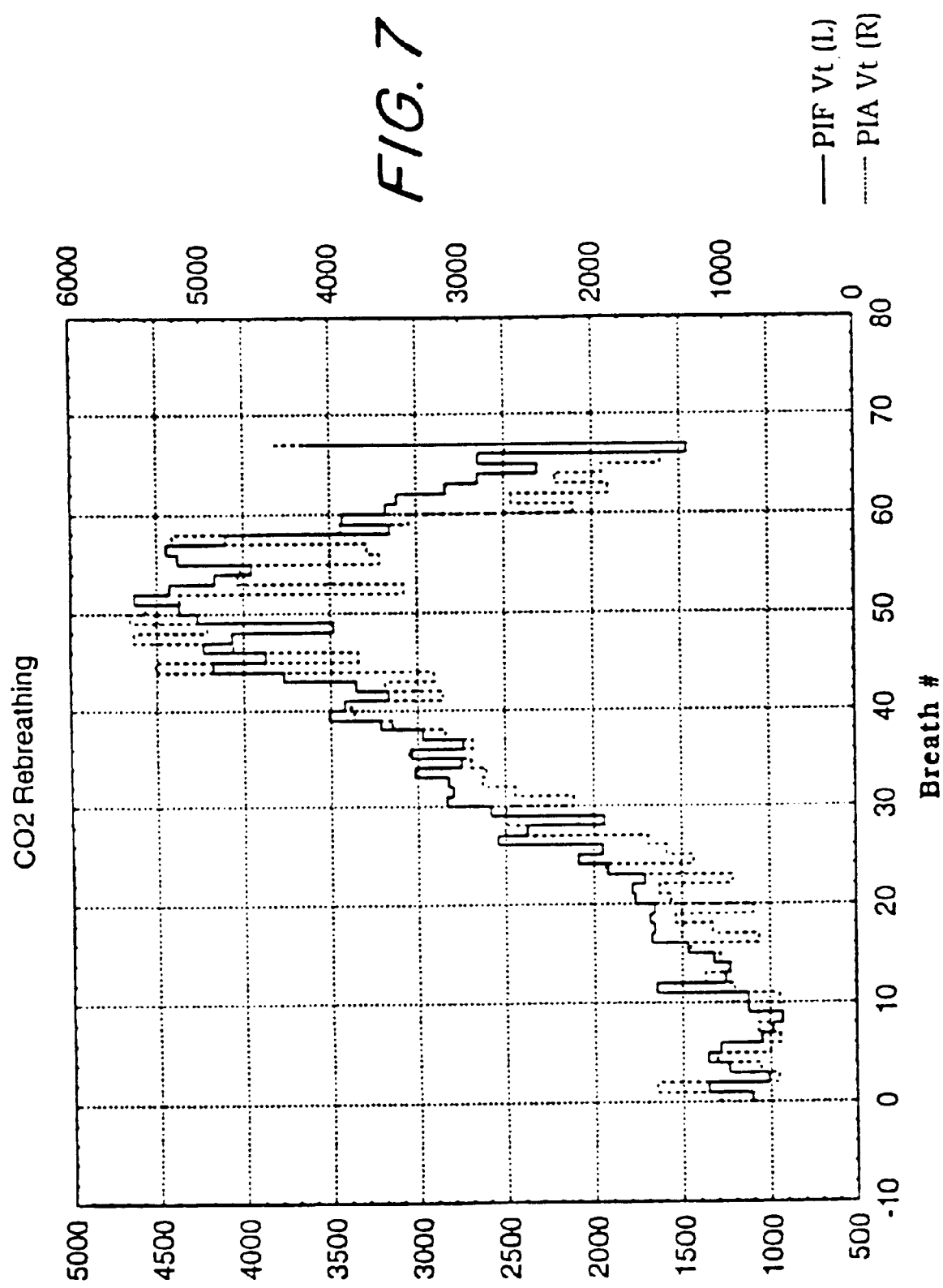
FIG. 7 is a graph plotting traces of peak inspiratory flow and acceleration parameters during $CO_2$ rebreathing.
Figure 8:
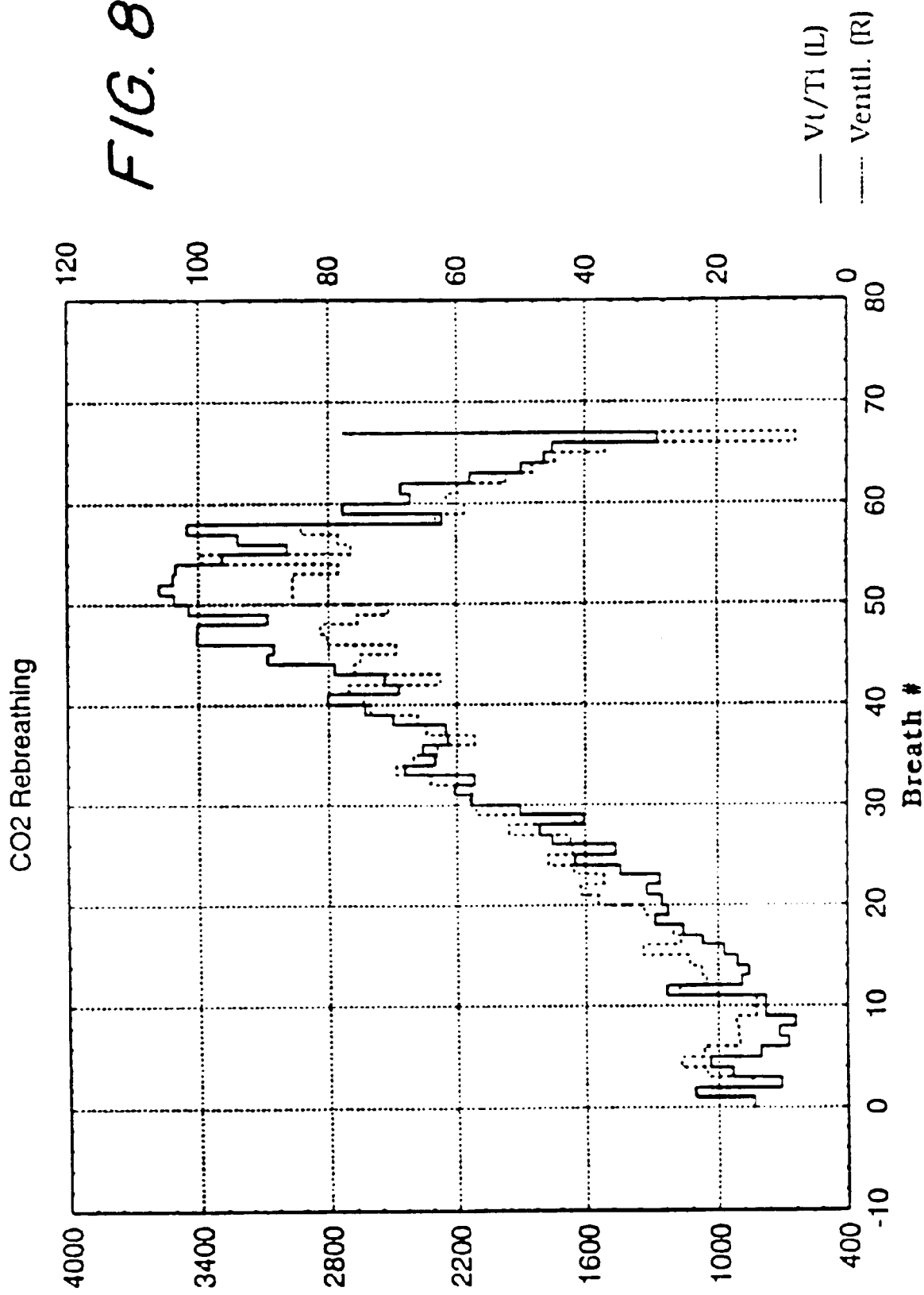
FIG. 8 is a graph plotting traces of mean inspiratory flow and ventilation during $CO_2$ rebreathing.

FIGS. 7 and 8 indicate the excellent correlation among measures of respiratory drive, e.g. PIF Vt, PIA Vt, Vt/Ti, and its output, i.e. ventilation.

Figure 9:
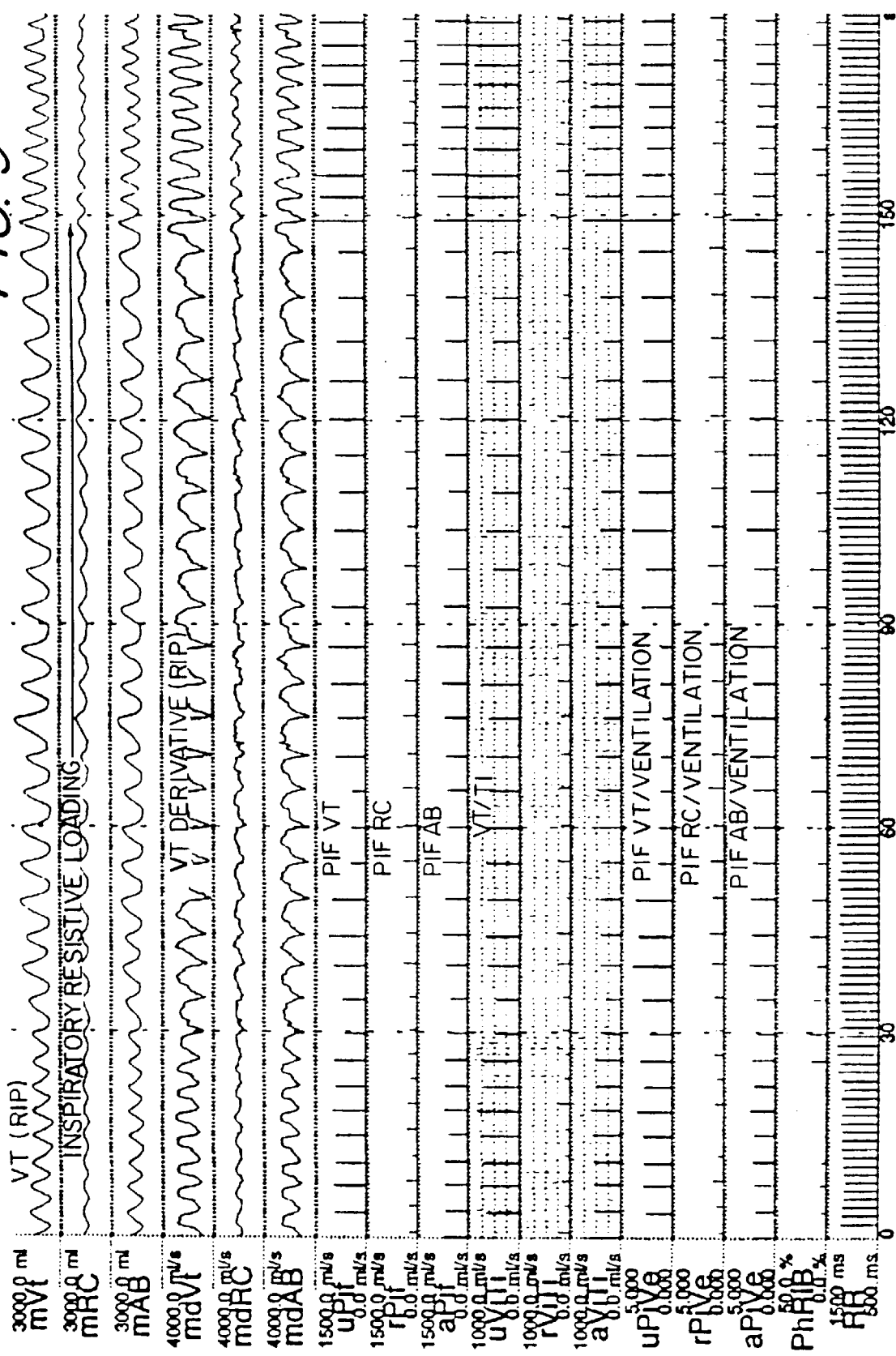
FIG. 9 is a graph plotting traces of peak inspiratory flow parameters during inspiratory resistive loading.
Figure 10:
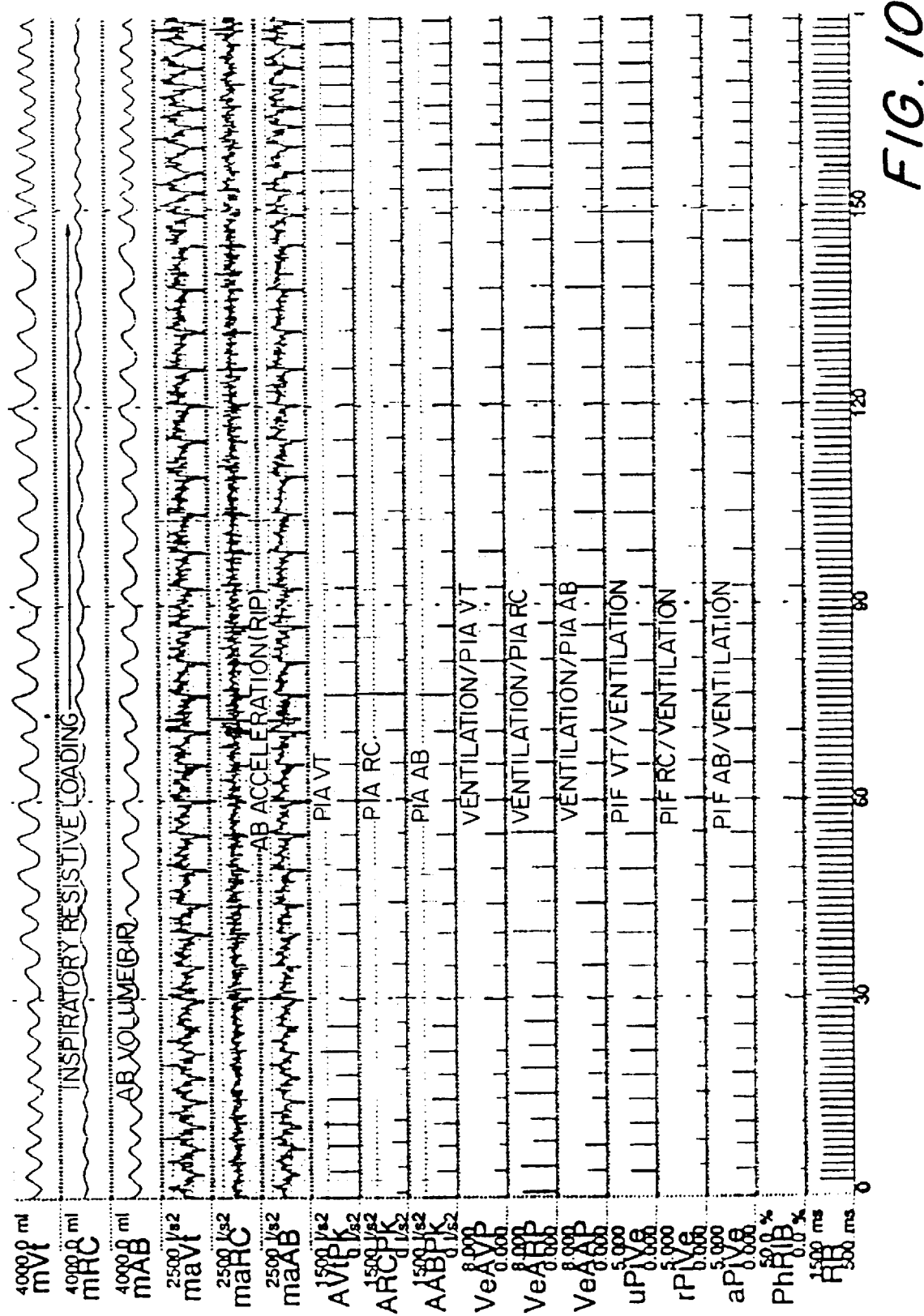
FIG. 10 is a graph plotting traces of peak inspiratory acceleration parameters during inspiratory resistive loading.

FIG. 9 shows that external inspiratory resistive loads up to 13 cm $H_2O/l/s$ did not affect peak inspiratory flow measures of drive nor ratios of drive to ventilation; in the recovery period, drive increased. FIG. 10 shows that inspiratory resistive loading decreased peak inspiratory acceleration measures of respiratory drive.

Figure 11:
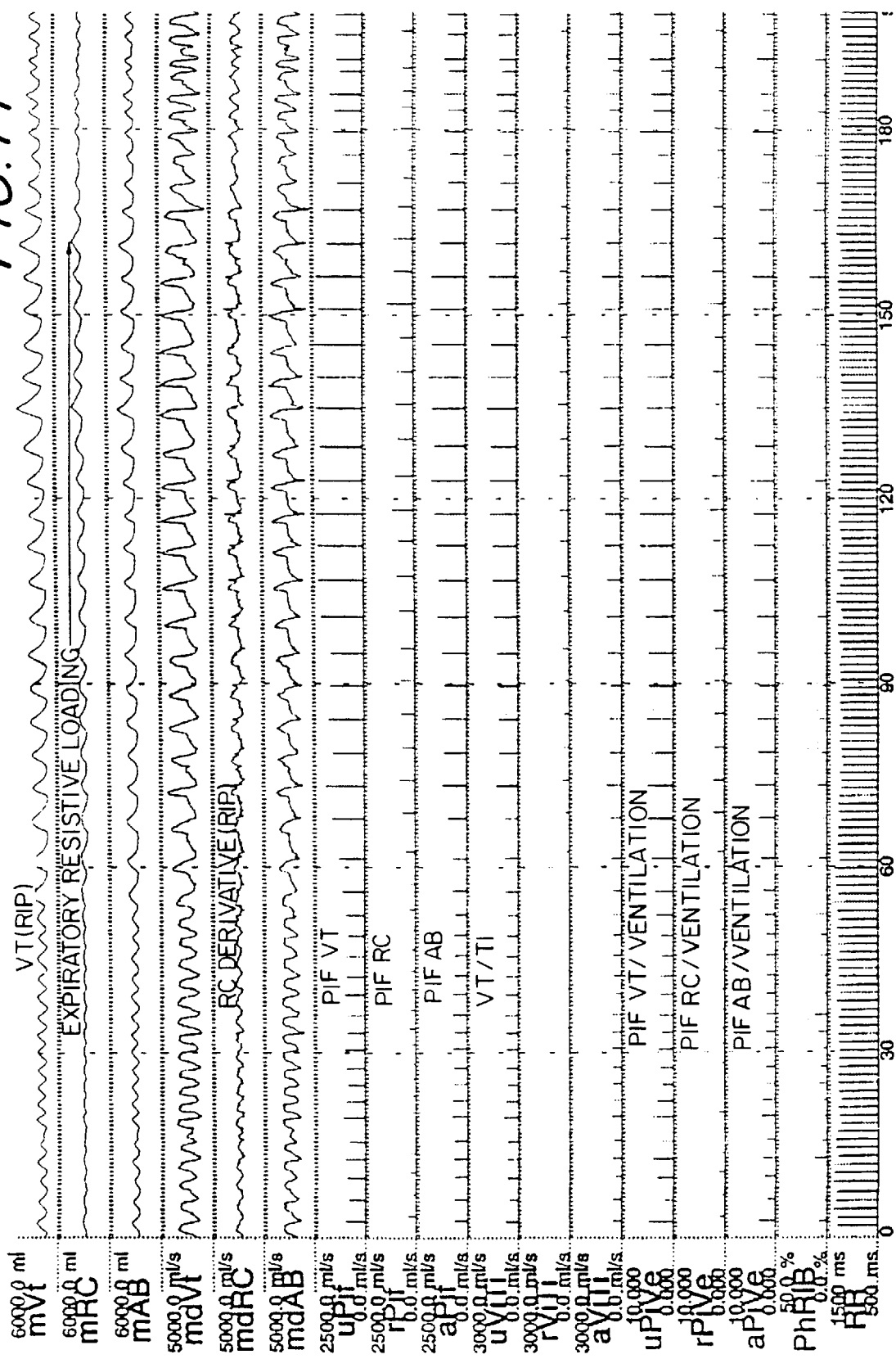
FIG. 11 is a graph plotting traces of peak inspiratory flow parameters during expiratory resistive loading.
Figure 12:
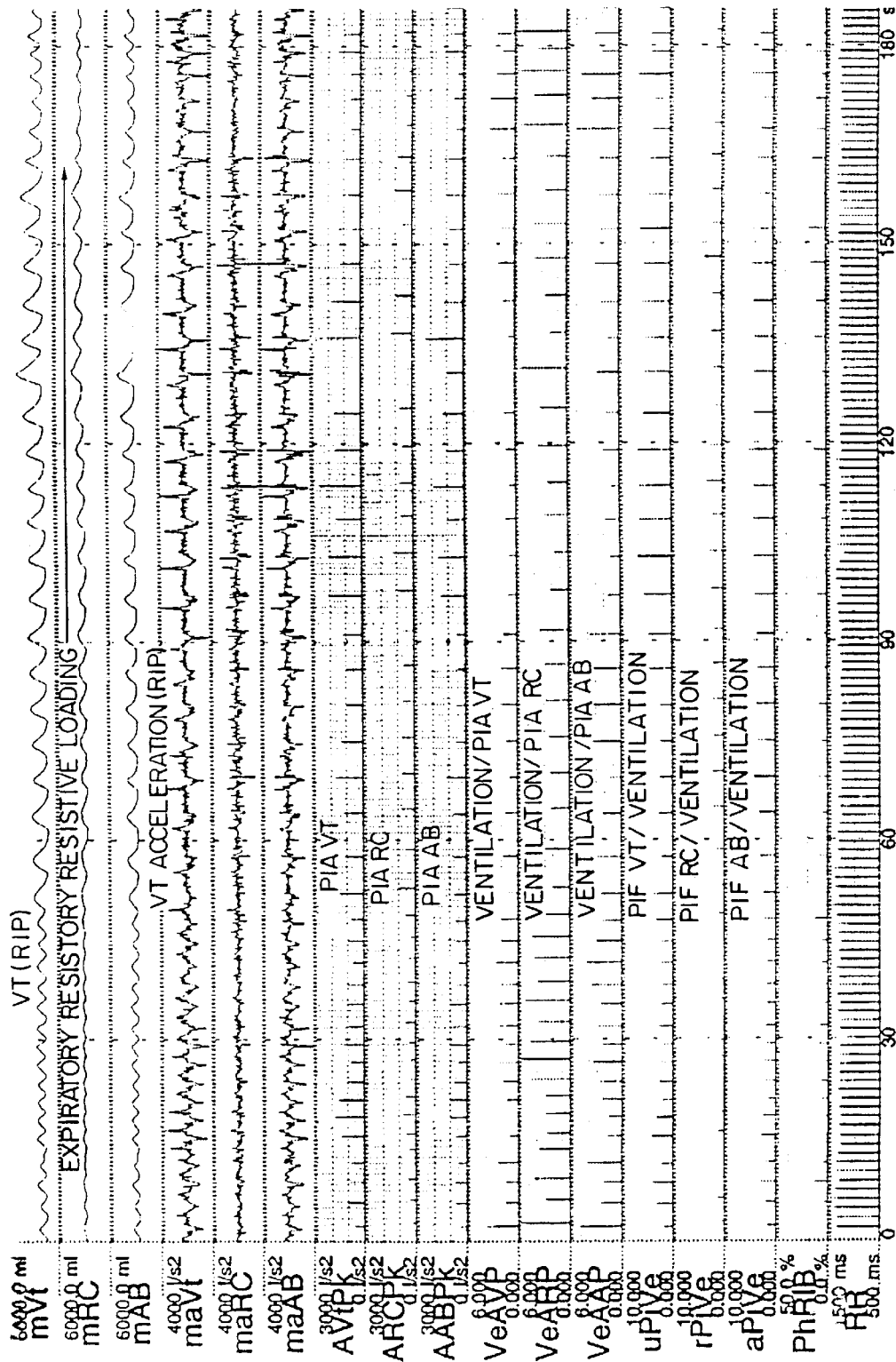
FIG. 12 is a graph plotting traces of peak inspiratory acceleration parameters during expiratory resistive loading.

Referring now to FIGS. 11 and 12, in contrast to external inspiratory loading, external expiratory resistive loading (13 cm $H_2O/l/s$) produced increased respiratory drive as evidenced by increases in both peak inspiratory flow (see FIG. 11) and acceleration (see FIG. 12) parameters. The ratios of drive to ventilation increased. In addition, there was a slight increase of the end expiratory lung volume level.

Figure 13:
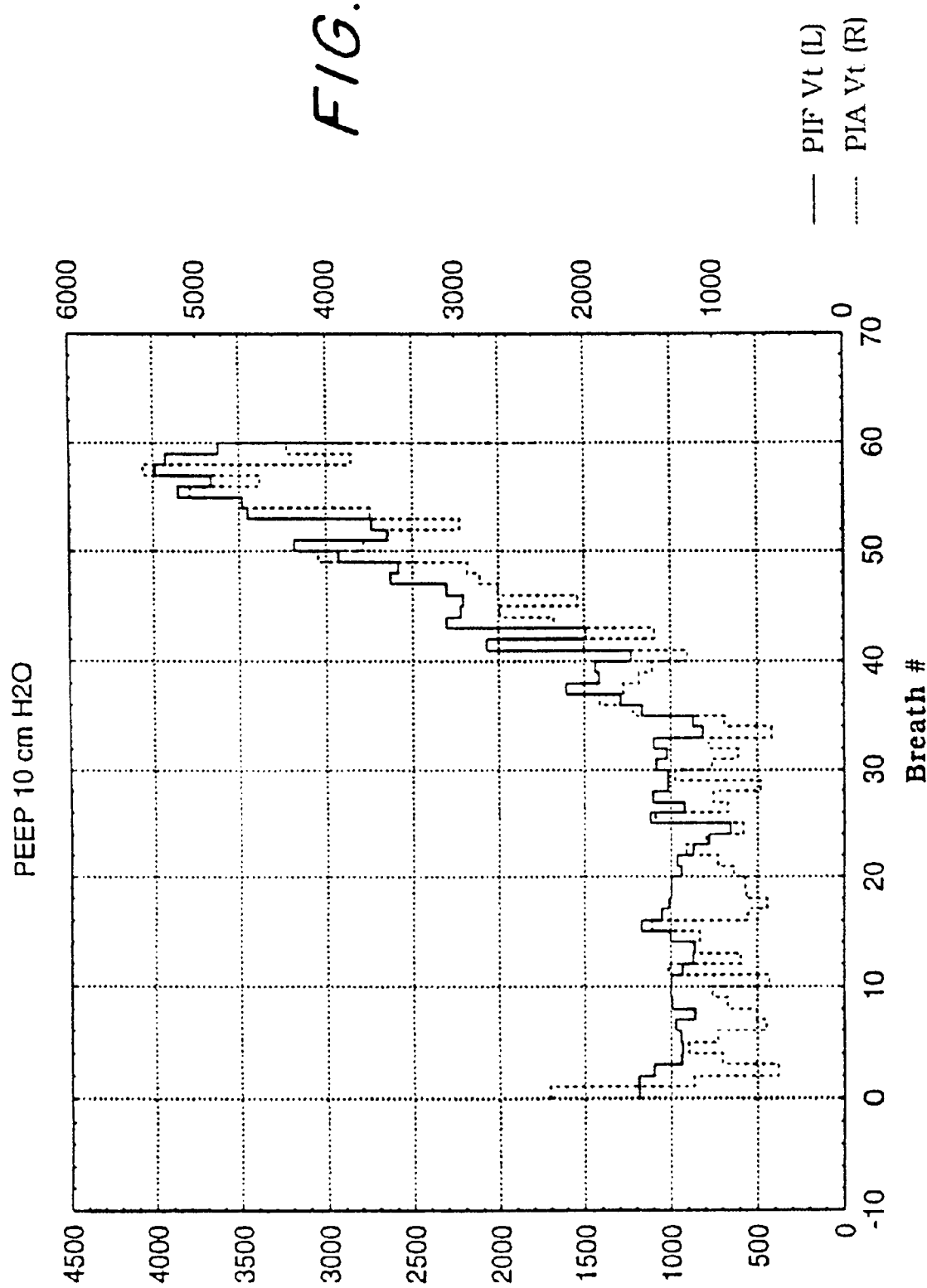
FIG. 13 is a graph showing traces of peak inspiratory flow and acceleration parameters with PEEP 10 cm H2O loading.
Figure 14:
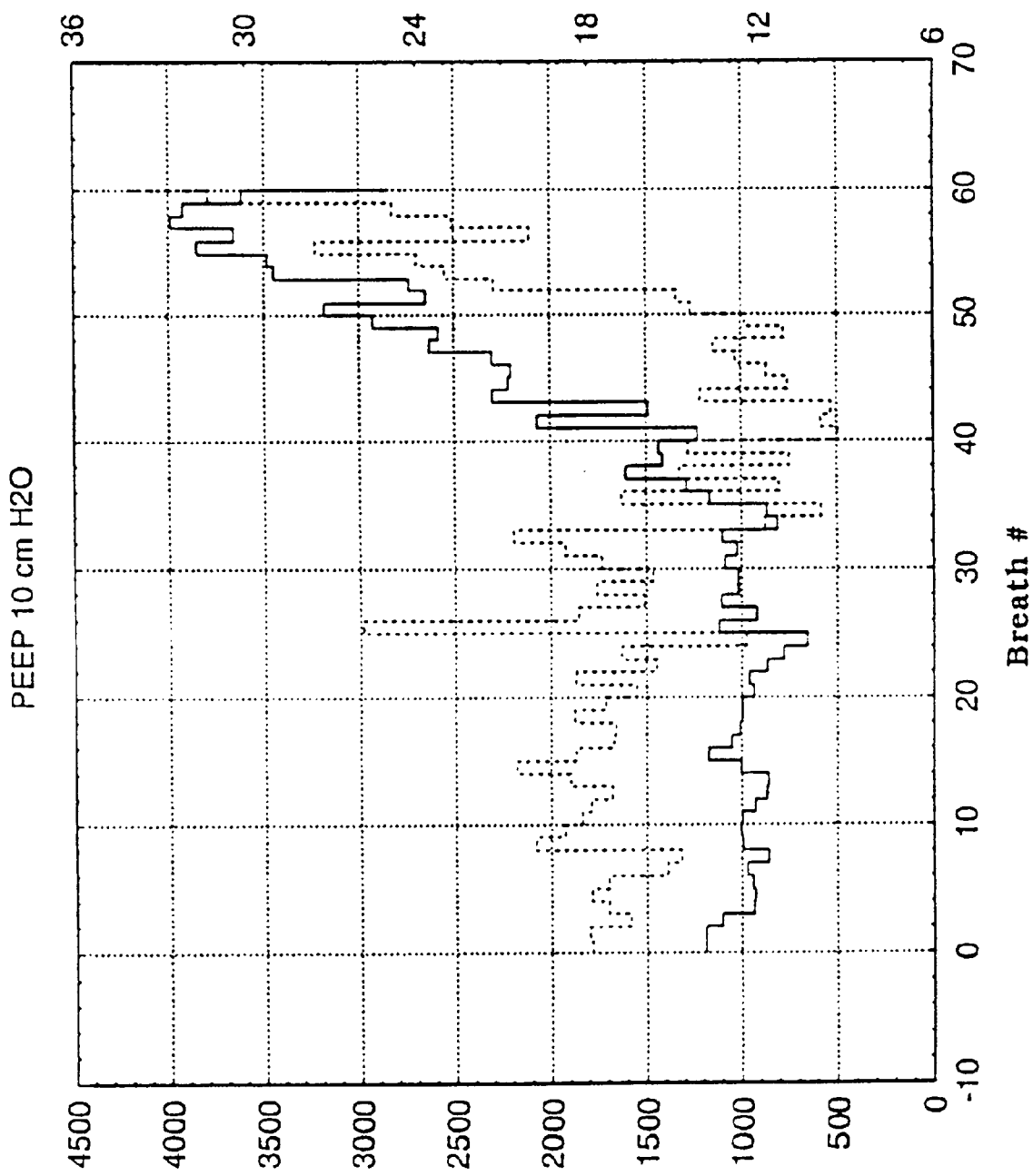
FIG. 14 is a graph depicting traces of peak inspiratory flow and ventilation during with PEEP 10 cm H2O loading.
Figure 15:
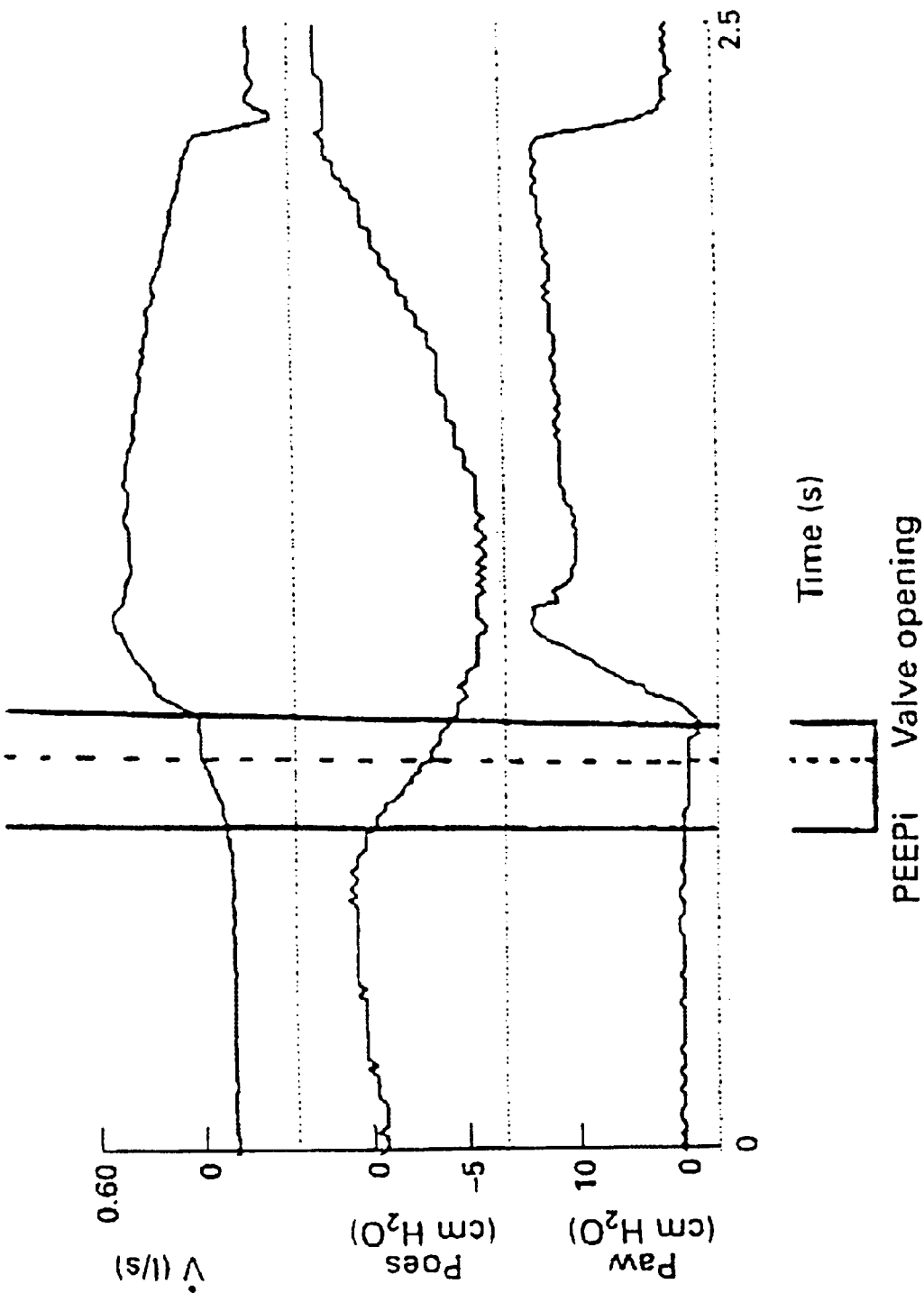
FIG. 15 is a timing diagram depicting phase triggering of a mechanical ventilator.

As shown in FIGS. 13 and 14, the application of 10 cm. $H_2O$ PEEP while the subject inspired air at atmospheric pressure produced significant elevation of end expiratory lung volume level that was accompanied by a progressive rise of drive measured either by peak inspiratory flow or acceleration parameters. There was a progressive, major increase of the drive to ventilation ratios indicating the extremely inefficient ventilatory response to the heightened drive associated with dynamic pulmonary hyperinflation. In addition, the RR interval (RR trace of recording) of the electrocardiogram decreased during the last one third of PEEP application indicating a significant rise of heart rate. Subjects voluntarily removed themselves from breathing through the mouthpiece to the PEEP valve within two to three minutes because breathlessness became intolerable. The heart rate as expressed by the fall of the RR interval of the electrocardiogram (see FIG. 12) rose in the last third of PEEP application, an objective sign of the sympathetic nervous system stress of pulmonary hyperinflation. This experimental model is analogous to pulmonary emphysema, which is also accompanied by pulmonary hyperinflation, increased respiratory drive, and an increased ratio of drive to ventilation.

In a study entitled *"Respiratory Drive During Carbachol Challenge in Allergic Sheep"* (T Stromberg, J. A Adams, W. M Abraham and M. A Sackner), fourteen unanesthetized sheep inhaled aerosolized saline as a control and then carbachol until bronchoconstriction to a threshold level took place.

This study, the results of which are summarized in Table 9, indicates that peak inspiratory acceleration and therefore respiratory drive increases in bronchoconstriction. The phenomenon can be detected with either respiratory inductive plethysmographic or pneumotachographic measurement of flow at the airway.

In addition to the original investigations for validating peak inspiratory flow and acceleration as measures of respiratory drive as herein described, there are other situations in which respiratory drive is altered. In such situations other methods—such as diaphragmatic electromyogram, occlusion pressures (P0.1), mean inspiratory flow, and ratio of esophageal pressure as a fraction of maximum inspiratory pressure (Pes divided by %PImax)—have been used as markers of drive. Example of such other situations are now discussed.

Respiratory Muscle Fatigue. This condition is diagnosed by the presence of increased respiratory drive in association with reduced ventilatory output due to failure of or ineffective respiratory muscle contractions. In its early stages, arterial carbon dioxide is reduced but later, arterial carbon dioxide is retained. If left untreated, respiratory arrest and death ultimately ensue. This sequence has been produced experimentally with a model of septic shock in anesthetized dogs. Diaphragmatic electromyogram, phrenic neurogram, and tracheal occlusion pressures were used to monitor drive. Transdiaphragmatic pressure was used to mark the contractile state of the diaphragmatic muscle and minute ventilation as its output measure. Respiratory muscle fatigue in dysfunction has also been found in hemorrhagic shock, during acute exacerbation of ventilatory insufficiency in patients with chronic obstructive pulmonary disease, and in patients with pulmonary edema.

Pulmonary Embolism. Experimental pulmonary embolism produces rapid shallow breathing, a finding attributed to reflex stimulation of the respiratory center. Clinically, dyspnea (which is uncomfortable breathlessness) and tachypnea (rapid respiratory rate) are common. Although values of respiratory drive have not been reported in pulmonary embolism, it is extremely likely that it accounts for both dyspnea and tachypnea.

Acute Pulmonary Edema. The breathing pattern in this condition associated with heart failure or Adult Respiratory Distress Syndrome is marked by increased respiratory rate, variable values of tidal volume, and elevated minute ventilation. Respiratory drive is increased. If elastic loading becomes excessive because of the stiff lungs due to fluid accumulation, then respiratory muscle fatigue develops with continued drive but decreased ventilation.

Asthma. Mean inspiratory flow, a measure of drive, increases during bronchospasm caused by reflux of gastric acid to the lower esophagus during sleep in asthmatic children. Furthermore, dynamic lung inflation contributes importantly to acute breathlessness during induced asthma, particularly at higher levels of bronchoconstriction. This seriously compromises the ability of inspiratory muscles to generate pressure, and adds substantial elastic and inspiratory threshold loads to muscles already burdened by the resistive loading of bronchospasm. The inspiratory threshold load (ITL) subsequent to dynamic hyperinflation (DH) means that the inspiratory effort generated at the onset of each breath is unrewarded until the opposing inward recoil pressure of the chest wall and lungs at end-expiration is overcome. Further, bronchoconstriction was associated with increased respiratory drive as measured by the ratio of esophageal pressure (Pes) divided by %PImax, a means to standardize Pes values.

Central Sleep Apnea of Heart Failure. Patients with stable, treated heart failure, with ejection fraction less than 45%, were classified awake as eucapnic (Pa $CO_2$ >35 and <44) and hypocapnic (Pa $CO_2$ <35). The presence of central apnea and hypopnea, and hourly occurrences of ventricular tachycardia, were significantly greater in hypocapnic than eucapnic patients. Hypocapnic patients had significantly more arousals and decreased sleep efficiency due to excessive periodic breathing. The positive predictive value of a low wake Pa $CO_2$ for central sleep apnea was 78%. The prevalence of ventricular tachycardia was twenty times greater in hypocapnic than eucapnic patients with chronic heart failure. The hypocapnic patients presumably have increased respiratory drive during the waking state to account for the low Pa $CO_2$.

Depression of Respiratory Drive. Measurement of respiratory drive can be utilized to gauge the effectiveness of narcotics and sedatives in decreasing drive where it is excessively elevated as in certain patients with restrictive and obstructive lung diseases.

Excessive Tracheobronchial Secretions. Respiratory drive is increased in patients that have excessive retention of tracheobronchial secretions. Monitoring its values helps to decide upon measures to improve tracheobronchial toilet, e.g. suctioning, postural drainage, etc.

Weaning From Mechanical Ventilator Support. Increased respiratory drive as measured with P0.1 is found in COPD patients with ventilatory insufficiency that requires mechanical ventilator support. The measure can be used for the timing of weaning from ventilatory support. If drive remains elevated over the days that weaning is considered, then the likelihood is that if the patient is removed from the ventilator, he/she will require reintubation and return to the ventilator shortly thereafter. If on the other hand respiratory drive falls, then the likelihood is that permanent removal from the mechanical ventilator will be successful.

CPAP for Ventilatory Support. mtaEDi (diaphragmatic electromyogram) activity is increased in patients with severe COPD FEV1.0=20% predicted normal. Such patients have intrinsic PEEP equivalent to 2.6 cm. $H_2O$. Addition of external PEEP decreased intrinsic PEEP and mtaEDi. These data suggest that measurement of respiratory drive can be used to guide the magnitude of extrinsic PEEP necessary to achieve effective ventilatory support. Dynamic lung hyperinflation is an important contributor to acute breathlessness during induced asthma, particularly at higher levels of bronchoconstriction. This seriously compromises the ability of inspiratory muscles to generate pressure and adds substantial elastic and inspiratory threshold loads to muscles already burdened by the resistive loading of bronchospasm. The inspiratory threshold load (ITL) subsequent to dynamic hyperinflation (DH) means that inspiratory effort generated at the onset of each breath is unrewarded until the opposing inward recoil pressure of the chest wall and lungs at end-expiration is overcome. This phenomenon takes place in mechanically ventilated COPD patients with ventilatory failure, as evidenced by intrinsic PEEP. Application of external continuous positive airway pressure (CPAP) improves patient comfort and relieves breathlessness by enhancing the triggering sensitivity of the ventilator. Since intrinsic PEEP is accompanied by an increased respiratory drive and drive to ventilation ratio, qualitative monitoring to detect intrinsic PEEP can be accomplished.

In general, although the results from analysis of peak inspiratory acceleration paralleled those from peak inspiratory flow during the aforedescribed experiments, acceleration values were more variable than flow values. This was due to the relatively slow digital sampling rate of the proprietary inductive plethysmographic hardware. Heretofore available hardware samples the transducer signal at 50 points/s, thereby filtering out some of the true peak values of acceleration. New electronic circuitry has now been developed to allow digital sampling rates to 200 points/s to obviate this problem, thereby improving the measurement accuracy of peak inspiratory flow and acceleration values. The rapid sampling rate enables accurate display of inductive plethysmography monitored breath waveforms during high frequency ventilation (respiratory strokes between 4 and 15 Hz). The system can serve as a rapid response trigger to initiate inspiratory inflation by mechanical ventilator devices. The system improves timing accuracy of inductive plethysmographic measurements of ventricular volume, systolic time intervals, and carotid and internal jugular venous pulses.

The base frequencies of inductive plethysmographic transducers are determined by the inductance of the transducer and the resistance and capacitance of the oscillator circuitry. Each of these parameters may be independently adjusted. For example, increasing the number of turns of the transducer around the body part being monitored, e.g. the RC, AB or neck, changes the oscillatory frequency of the signal and improves the signal-to-noise ratio. By maximizing differences in oscillatory signal frequencies between transducers, one can minimize electrical cross talk between transducers and thereby also increase the signal-to-noise ratio between adjacent inductive plethysmographic sensors. Another source of electrical noise in the inductive plethysmographic signal is the cable carrying the undemodulated signal to a demodulator module; this noise is minimized by locating the oscillators directly on the transducer band with the inductive plethysmographic hardware capable of accepting any number of oscillator generated signals. Preliminary studies confirm that these hardware and transducer operation modifications and improvements produce more consistent peak inspiratory flow and acceleration values.

The heretofore presently commercially available inductive plethysmographic hardware translates transducer inductance changes to a signal that corresponds linearly to changes in cross sectional area underneath the band, at a rate of 50 Hz. The signal-to-noise ratio is approximately 100 to 1 when the "signal" is a normal breath.

To increase the data sampling rate from 50 points/s to 200 points/s, the band frequency divider was reduced from 4096 cycles to 1024 cycles; the band oscillation frequency remained the same. To preserve and actually improve the signal-to-noise ratio, two steps were taken. First, the oscillation period counter was increased from 10 MHz to 40 MHz, keeping the oscillation period resolution the same as in the 50 points/s hardware. Second, the isolation pot cores used in the prior inductive plethysmographic hardware were replaced with high performance toroids. The response of the then-existing pot cores was found to be insufficient for accomplishing accurate sampling in the new 5 ms (200 Hz) window; the new toroids yielded a better signal-to-noise ratio at 200 Hz than the pot cores achieved at 50 Hz.

The heretofore commercially available inductive plethysmographic hardware utilizes Phillips 1408PL00-3B9 pot cores. In the inventive rapid responsive system, these were changed to Phillips 768XT188-3F3 toroids. The change in material (from 3B9 to 3F3) increased manufacturing difficulty, which is nevertheless offset by the increase in gain.

The digital circuitry of the hardware was also updated, changing from 74 series CMOS logic to an integrated field programmable gate array (FPGA) (Phillips PZ5128-S10A84). This single FPGA contains all of the digital logic for two inductive plethysmographic channels and also has leftover capacity that serves as glue logic for the microcontroller. The microcontroller is now integrated onto the same printed circuit card as the inductive plethysmographic channels, realizing for the first time a single card QDC calibratable inductive plethysmographic solution. Utilization of surface mount technology and integrated FPGA reduced the size of this single card to approximately half the size of the previous inductive plethysmographic hardware card which did not include the microprocessor, a component that is necessary for QDC calibration and generation of analog outputs. The inventive two channel inductive plethysmographic channel system is expandable up to eight channels by keeping each oscillator on a separate base frequency to avoid electrical crosstalk. This is implemented by replicating the two-channel system, or using a higher density FPGA along with a higher performance microcontroller, so that additional inductive plethysmographic channels are placed on the single card.

As indicated above, triggering technologies at the airway site from flow or pressure sensors will always be delayed relative to the patient's own initiation of inspiration. This delay is accentuated to a great length during intense resistive loading intense resistive loading as demonstrated in FIG. 16.

In that Figure the airway sensor, which is an integrated pneumotachograph, is greatly delayed relative to the standard for initiation of inspiration, i.e., esophageal or transpulmonary pressure. This has engendered research on triggering sensors placed on the body surface but the technologies employed, e.g. impedance pneumography or the Graseby capsule, are unreliable. The Graseby capsule has not shortened the delay of flow triggered systems, probably because the capsule triggers from localized movement of the abdominal wall rather than from the overall abdominal or rib cage respiratory signal.

Figure 16:
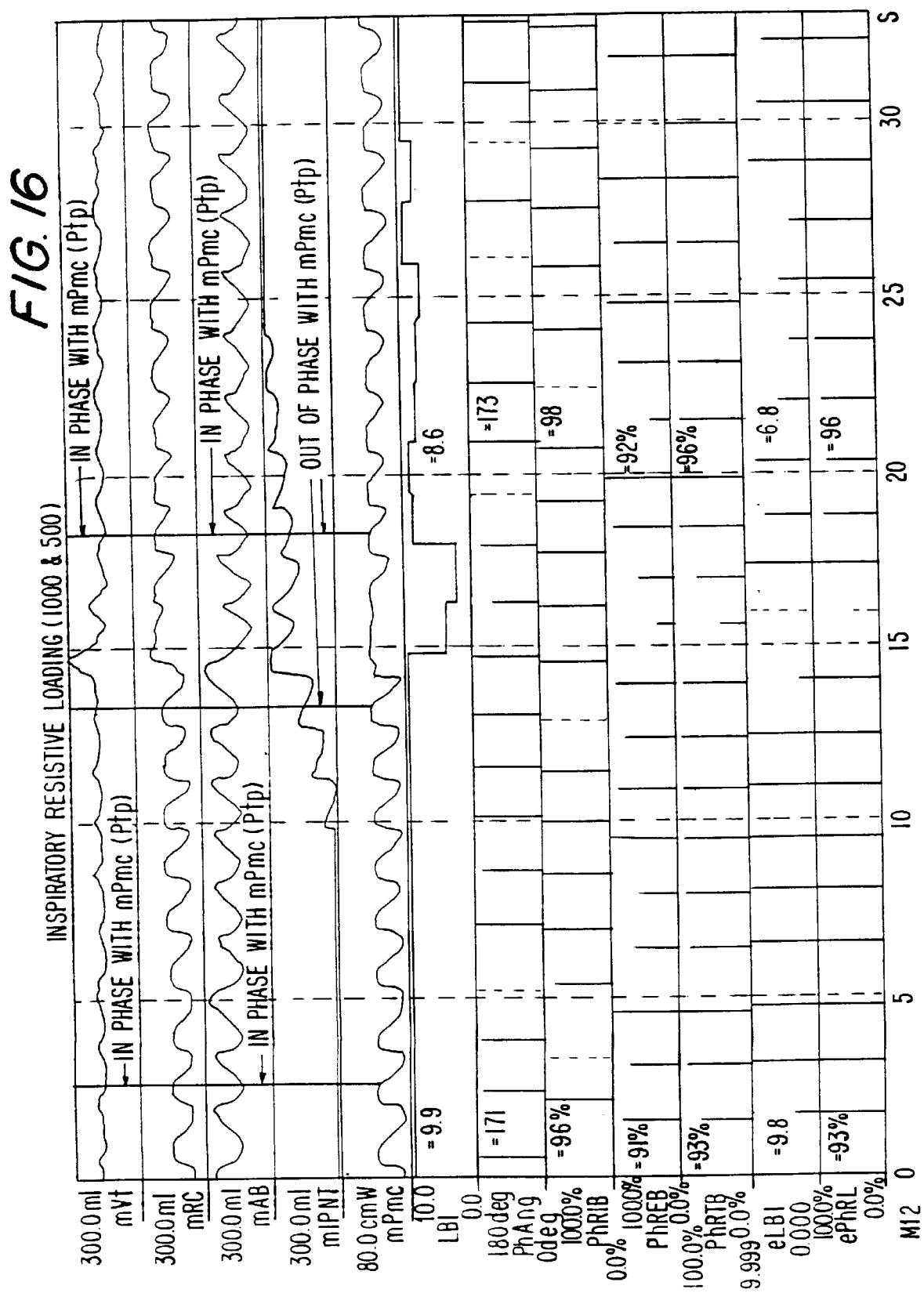
FIG. 16 is a recording of extrinsic inspiratory resistive loads applied to an anesthetized monkey that illustrates the error in timing that would occur if mechanical ventilators were triggered by sensors placed at the airways.

The inventive rapid response respiratory inductive plethysmograph appears to fulfill the heretofore unmet needs for rapid triggering because it is close to esophageal pressure. The trigger threshold can be semi-quantitative based upon percent baseline volume, or quantitative based upon ml volume or ml/s flow. The trigger pulse can originate from the leading compartment of the rib cage or abdomen. In FIG. 16, the abdominal expansion (AB) measured with respiratory inductive plethysmography most consistently tracked Ptp and could provide a noninvasive waveform for triggering mechanical ventilation if needed in this situation.

In the preferred embodiment, the rapid response respiratory inductive plethysmograph system (resolution to 200 points/s) controls the initiation of inspiratory inflation of mechanical ventilators by transmitting a pulse to them when either a volume, flow or acceleration threshold is exceeded. In a less preferred embodiment, the heretofore available respiratory inductive plethysmographic system (resolution to 50 points/s) controls the initiation of inspiratory inflation of mechanical ventilators by transmitting a pulse to the ventilators when either a volume, flow or acceleration threshold is exceeded. The trigger pulse is generated when is either a volume, flow, or acceleration threshold is exceeded from either the rib cage or abdominal compartment waveform, depending upon which is leading the other. Compartment selection for triggering may be performed manually or automatically by the computer.

Another purpose of the present invention is to eliminate or minimize the limitations of the pneumotachograph primary sensor within current CPAP devices by using the respiratory inductive plethysmograph as its controller. Other respiratory monitoring devices in which transducers placed over the rib cage and abdomen can be calibrated quantitatively to monitor respiratory volumes and detect apneas/hypopneas may serve as less preferred alternatives. The index of peak inspiratory flow (PIF) divided by mean inspiratory flow (MIF) is computed from the respiratory inductive plethysmographic tidal volume breath waveforms, breath by breath, as a measure of inspiratory flow shape in a similar way as has been computed by others for the pneumotachograph flow waveform. MIF must be computed from the value of the integral above an arbitrary flow threshold from the flow waveform, not from tidal volume divided by inspiratory time; this is because normal pauses with zero flow or extremely low flow rates within the breath might be included as part of inspiratory time owing to uncertainties as to where inspiration begins. For example, if there is an expiratory pause of one second, part of it could unintendedly be included within inspiratory time and thereby lead to spuriously low values of the ratio PIF/MIF.

Sinusoidal shaped inspiratory flow waveforms that are indicative of unobstructed breathing have PIF/MIF values of $\pi/2=1.57$. A perfect rectangularly shaped, inspiratory flow waveform has a PIF/MIF value of 1.0. Significant flattening from a sinusoidal shape is present at a PIF/MIF value of about 1.3 and below. In some instances, partial obstruction is associated with very high peak inspiratory flows such that values of PIF/MIF are greater than about 1.85. Thus, values of PIF/MIF less than 1.3 and greater than 1.85 call for increasing the level of CPAP administered manually or with a delay in a servo control system to maintain PIF/MIF within the optimal range of approximately 1.31–1.84.

In addition, the same algorithm for computation of PIF/MIF can be applied to the expiratory flow waveforms. The shape significance for expiratory airway obstruction is the same as for inspiratory airway obstruction. MEF must be computed from the value of the integral above an arbitrary flow threshold from the flow waveform, not from tidal volume divided by expiratory time; this is because normal pauses with zero flow or extremely low flow rates within the breath might be included as part of expiratory time owing to uncertainties as to where expiration ends. For example, if there is an expiratory pause of one second, all or part of it could unintendedly be included as expiratory time and thereby lead to spuriously low values of the ratio PEF/MEF. Values of PEF/MEF less than 1.3 and greater than 1.85 call for increasing the level of CPAP administered manually or with a delay in a servo control system to maintain PEF/MEF within the optimal range of approximately 1.31–1.84.

In addition to utilization of the shape of inspiratory and/or expiratory flow waveforms to control the level of CPAP, respiratory drive and the ratio of respiratory drive to ventilation can be utilized as confirmation indicators or as stand-alone markers of resistive loading. Such measures as peak inspiratory flow and acceleration have been described herein as measures of drive that are increased by resistive loading. The ratio of drive to ventilation permits secondary adjustment of CPAP pressures delivered to the patient. The level of CPAP may also be altered based upon the frequency of obstructive apneas and hypopneas detected by the respiratory inductive plethysmograph. The plethysmograph may be programmed to avoid changing CPAP or to alter it in the presence of central apneas and hypopneas.

Finally, drive and drive to ventilation ratio measures can be used to detect elevations of inspiratory threshold load due to dynamic hyperinflation produced by acute bronchospasm. This condition can be corrected by applying CPAP to lower the drive and the drive to ventilation ratio.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

TABLE 1

Peak Acceleration, Mean Inspiratory Flow and Ventilation during $CO_2$ Rebreathing in Sixteen Healthy Preterm Infants

| State | Peak Inspiratory Acceleration Vt (PIA Vt) | | | Peak Inspiratory Acceleration RC (PIA RC) | | | Peak Inspiratory Acceleration AB (PIA AB) | | | Mean Inspiratory Flow (Vt/Ti) | | |
|---|---|---|---|---|---|---|---|---|---|---|---|---|
| | Baseline | $CO_2$ | Difference | Baseline | $CO_2$ | Difference | Baseline | $CO_2$ | Difference | Baseline | $CO_2$ | Difference |
| Active | 268 | 565 | 296 | 255 | 479 | 223 | 253 | 437 | 183 | 32 | 56 | 24 |
| Quiet | 182 | 716 | 534 | 138 | 426 | 288 | 162 | 519 | 357 | 27 | 60 | 33 |
| Difference p | <.05 | n.s. | <.002 | <.01 | n.s. | n.s. | <.01 | n.s. | <.002 | <.05 | n.s. | n.s. |

TABLE 2

Respiratory Drive (Peak Inspiratory Acceleration) to Ventilation Ratios during $CO_2$ Rebreathing in Sixteen Healthy Preterm Infants

| State | Peak Inspiratory Acceleration (PIA)Ventilation | | |
|---|---|---|---|
| | Baseline | $CO_2$ | Difference |
| Active | 332 | 398 | 66 |
| Quiet | 262 | 452 | 189 |
| Difference p | n.s. | n.s | <.001 |

TABLE 3

Correlation Coefficients, r, Among Breath Waveforms from Respiratory Inductive Plethysmograph and Moving Time Average of Diaphragmatic Electromyogram During $CO_2$ Rebreathing; Flow Parameters (Nine Piglets)*

| | No. Breaths Analyzed | No. Breaths Deleted | r (Ventil vs EdiA/Ti) | r(PIF Vt vs EdiA/Ti) | r(PIF RC vs EdiA/Ti) | r(PIF AB vs EdiA/Ti) | r(EdiPS vs EdiA/Ti) | r(Vt/Ti vs EdiA/Ti) | r(RC/Ti vs EdiA/Ti) | r(AB/Ti vs EdiA/Ti) | r(Edia vs EdiA/Ti) | r(Ventil vs EdiA) |
|---|---|---|---|---|---|---|---|---|---|---|---|---|
| p11sc  | 187 |    | 0.81 | 0.77 | 0.35 | 0.28 | 0.96 | 0.54 | 0.25 | 0.21 | 0.20 | -0.07 |
| p11scd | 176 | 11 | 0.76 | 0.76 | 0.25 | 0.64 | 0.79 | 0.62 | 0.03 | 0.64 | -0.48 | -0.51 |
| p11pc  | 203 |    | 0.43 | 0.35 | 0.35 | 0.03 | 0.93 | 0.20 | 0.22 | 0.05 | 0.94 | 0.50 |
| p11pcd | 182 | 21 | 0.59 | 0.66 | 0.06 | 0.44 | 0.65 | 0.62 | 0.08 | 0.53 | 0.48 | 0.12 |
| p13sc  | 344 |    | 0.68 | 0.71 | 0.70 | 0.51 | 0.92 | 0.67 | 0.68 | 0.29 | 0.85 | 0.77 |
| p13scd | 326 | 18 | 0.91 | 0.93 | 0.92 | 0.90 | 0.96 | 0.93 | 0.92 | 0.88 | 0.95 | 0.95 |
| p13pu  | 268 |    | 0.58 | 0.41 | 0.45 | 0.32 | 0.67 | 0.32 | 0.32 | 0.13 | 0.83 | 0.47 |
| p13pud | 238 | 30 | 0.86 | 0.81 | 0.81 | 0.59 | 0.84 | 0.79 | 0.80 | 0.52 | 0.88 | 0.82 |
| p14sc  | 252 |    | 0.76 | 0.67 | 0.78 | 0.76 | 0.76 | 0.71 | 0.70 | 0.70 | 0.83 | 0.79 |
| p14scd | 250 | 2  | 0.78 | 0.80 | 0.82 | 0.80 | 0.81 | 0.71 | 0.72 | 0.71 | 0.85 | 0.79 |
| p14pc  | 260 |    | 0.76 | 0.88 | 0.75 | 0.30 | 0.83 | 0.66 | 0.77 | 0.44 | 0.85 | 0.87 |
| p14pcd | 257 | 3  | 0.85 | 0.76 | 0.86 | 0.37 | 0.85 | 0.81 | 0.89 | 0.55 | 0.92 | 0.87 |
| p14pu  | 234 |    | 0.60 | 0.66 | 0.58 | 0.73 | 0.75 | 0.72 | 0.62 | 0.76 | 0.69 | 0.71 |
| p14pud | 231 | 3  | 0.82 | 0.87 | 0.82 | 0.64 | 0.90 | 0.80 | 0.85 | 0.61 | 0.92 | 0.74 |
| p15sc  | 192 |    | 0.73 | 0.70 | 0.55 | 0.70 | 0.84 | 0.64 | 0.55 | 0.25 | 0.80 | 0.77 |
| p15scd | 174 | 18 | 0.80 | 0.80 | 0.72 | 0.78 | 0.70 | 0.74 | 0.72 | 0.25 | 0.85 | 0.79 |
| p21sc  | 182 |    | 0.61 | 0.54 | 0.65 | 0.78 | 0.85 | 0.41 | 0.39 | 0.38 | 0.84 | 0.67 |
| p21scd | 167 | 15 | 0.72 | 0.50 | 0.47 | 0.63 | 0.50 | 0.54 | 0.65 | 0.52 | 0.74 | 0.85 |
| p21pc  | 220 |    | 0.77 | 0.90 | 0.85 | 0.91 | 0.94 | 0.53 | 0.67 | 0.51 | 0.94 | 0.59 |
| p21pcd | 217 | 3  | 0.77 | 0.92 | 0.89 | 0.91 | 0.94 | 0.57 | 0.76 | 0.50 | 0.95 | 0.60 |
| p21pu  | 178 |    | 0.77 | 0.87 | 0.89 | 0.92 | 0.97. | 0.49 | 0.74 | 0.25 | 0.98 | 0.70 |
| p21pud | 178 | 0  | 0.77 | 0.87 | 0.89 | 0.92 | 0.97 | 0.49 | 0.74 | 0.25 | 0.98 | 0.70 |
| p22sc  | 147 |    | 0.80 | 0.64 | 0.71 | 0.70 | 0.95 | 0.62 | 0.41 | 0.48 | 0.95 | 0.72 |
| p22scd | 143 | 3  | 0.83 | 0.68 | 0.71 | 0.71 | 0.95 | 0.68 | 0.40 | 0.49 | 0.96 | 0.70 |
| p22pc  | 178 |    | 0.75 | 0.55 | 0.44 | 0.66 | 0.97 | 0.44 | 0.06 | 0.36 | 0.80 | 0.65 |
| p22pcd | 173 | 5  | 0.77 | 0.70 | 0.61 | 0.50 | 0.97 | 0.46 | 0.07 | 0.35 | 0.81 | 0.68 |
| p22pu  | 153 |    | 0.57 | 0.27 | 0.36 | 0.07 | 0.95 | 0.41 | 0.22 | -0.03 | 0.97 | 0.52 |
| p22pud | 144 | 9  | 0.78 | 0.27 | 0.40 | 0.11 | 0.96 | 0.46 | 0.19 | -0.02 | 0.97 | 0.70 |
| p23sc  | 172 |    | 0.86 | 0.79 | 0.75 | 0.84 | 0.90 | 0.77 | 0.79 | 0.44 | 0.85 | 0.82 |
| p23scd | 170 | 2  | 0.86 | 0.78 | 0.73 | 0.84 | 0.90 | 0.78 | 0.79 | 0.43 | 0.86 | 0.82 |
| p24sc  | 158 |    | 0.88 | 0.87 | 0.88 | 0.45 | 0.86 | 0.59 | 0.62 | 0.70 | 0.87 | 0.96 |
| p24scd | 149 | 9  | 0.97 | 0.95 | 0.95 | 0.64 | 0.98 | 0.64 | 0.62 | 0.67 | 0.99 | 0.97 |
| p24pc  | 149 |    | 0.35 | 0.54 | 0.63 | 0.81 | 0.79 | 0.08 | 0.12 | 0.81 | 0.80 | 0.43 |
| p24pcd | 137 | 12 | 0.88 | 0.93 | 0.88 | 0.94 | 0.95 | 0.87 | 0.71 | 0.87 | 0.95 | 0.92 |
| p24pu  | 125 |    | 0    | 0.18 | 0.23 | 0.81 | 0.87 | -0.04 | -0.04 | 0.04 | 0.13 | 0.10 |
| p24pud | 117 | 8  | 0.70 | 0.93 | 0.87 | 0.98 | 0.99 | 0.86 | 0.57 | 0.94 | 0.13 | -0.11 |
| p25sc  | 203 |    | 0.93 | 0.93 | 0.85 | 0.93 | 0.95 | 0.72 | 0.42 | 0.91 | 0.97 | 0.94 |
| p25scd | 196 | 7  | 0.96 | 0.93 | 0.84 | 0.93 | 0.94 | 0.71 | 0.65 | 0.91 | 0.96 | 0.96 |
| p25pc  | 245 |    | 0.94 | 0.96 | 0.93 | 0.95 | 0.97 | 0.87 | 0.88 | 0.89 | 0.96 | 0.88 |
| p25pcd | 245 | 0  | 0.94 | 0.96 | 0.93 | 0.95 | 0.97 | 0.87 | 0.88 | 0.89 | 0.96 | 0.88 |
| p25pu  | 188 |    | 0.88 | 0.94 | 0.94 | 0.95 | 0.97 | 0.17 | 0.52 | 0.79 | 0.97 | 0.81 |
| p25pud | 176 | 11 | 0.95 | 0.92 | 0.84 | 0.90 | 0.97 | 0.80 | 0.64 | 0.88 | 0.96 | 0.91 |

TABLE 3-continued

Correlation Coefficients, r, Among Breath Waveforms from Respiratory Inductive Plethysmograph and Moving Time Average of Diaphragmatic Electromyogram During CO$_2$ Rebreathing; Flow Parameters (Nine Piglets)*

| Mean** | 202 | | | | | | | | | | | | | | |
|---|---|---|---|---|---|---|---|---|---|---|---|---|---|---|---|
| SD** | 51 | | .82 .10 | .80 .17 | .73 .24 | | .72 .23 | .89 .12 | .70 .14 | | .60 .28 | .59 .26 | | .79 .35 | .67 .38 |
| | r(PIF Vt vs EdiA) | r(PIF RC vs EdiA) | r(PIF AB vs EdiA) | r(EdiPS vs EdiA) | r(Vt/Ti vs EdiA) | r(RC/Vi vs EdiA) | r(AB/Ti vs EdiA) | r(EdiA/Ti vs EdiA) | R(Ventil vs EdiPS) | r(PIF Vt vs EdiPS) | r(PIF RC vs EdiPS) | r(PIF AB vs EdiPS) | r(Vt Ti vs EdiPS) | r(RC/Ti vs EdiPS) | r(AB/Ti vs EdiPS) | r(EdiA/ Vt vs EdiPS) | R(EdiA vs EdiPS) |
| p11sc | -0.12 | -0.24 | -0.37 | 0.32 | -0.09 | 0.14 | -0.29 | 0.20 | 0.71 | 0.66 | 0.32 | 0.14 | 0.40 | 0.21 | 0.05 | 0.20 | 0.32 |
| p11scd | -0.52 | -0.44 | -0.44 | -0.40 | -0.27 | 0.04 | -0.30 | -0.48 | 0.60 | 0.62 | 0.20 | 0.52 | 0.39 | -0.10 | 0.49 | 0.79 | 0.40 |
| p11pc | 0.37 | 0.49 | 0.05 | 0.98 | 0.14 | 0.25 | -0.09 | 0.94 | 0.56 | 0.42 | 0.48 | 0.02 | 0.19 | 0.29 | -0.01 | 0.93 | 0.98 |
| p11pcd | 0.13 | 0.33 | -0.10 | 0.52 | -0.05 | -0.16 | -0.19 | 0.48 | 0.36 | 0.39 | 0.08 | 0.23 | 0.32 | 0.04 | 0.24 | 0.65 | 0.52 |
| p13sc | 0.75 | 0.73 | 0.61 | 0.93 | 0.69 | 0.71 | 0.35 | 0.85 | 0.65 | 0.65 | 0.64 | 0.55 | 0.61 | 0.62 | 0.31 | 0.92 | 0.93 |
| p13scd | 0.95 | 0.94 | 0.87 | 0.95 | 0.93 | 0.92 | 0.96 | 0.95 | 0.90 | 0.91 | 0.90 | 0.89 | 0.91 | 0.90 | 0.88 | 0.96 | 0.95 |
| p13pu | 0.34 | 0.45 | 0.13 | 0.83 | 0.17 | 0.13 | -0.06 | 0.83 | 0.37 | 0.28 | 0.32 | 0.19 | 0.18 | 0.17 | 0.02 | 0.67 | 0.83 |
| p13pud | 0.76 | 0.77 | 0.53 | 0.89 | 0.73 | 0.74 | 0.52 | 0.88 | 0.77 | 0.72 | 0.73 | 0.56 | 0.70 | 0.72 | 0.51 | 0.84 | 0.89 |
| p14sc | 0.80 | 0.87 | 0.86 | 0.90 | 0.65 | 0.77 | 0.70 | 0.83 | 0.75 | 0.82 | 0.86 | 0.87 | 0.66 | 0.73 | 0.68 | 0.76 | 0.90 |
| p14scd | 0.85 | 0.87 | 0.87 | 0.85 | 0.65 | 0.77 | 0.70 | 0.85 | 0.75 | 0.86 | 0.86 | 0.88 | 0.67 | 0.76 | 0.69 | 0.81 | 0.91 |
| p14pc | 0.91 | 0.96 | 0.44 | 0.94 | 0.71 | 0.90 | 0.61 | 0.85 | 0.81 | 0.91 | 0.90 | 0.40 | 0.66 | 0.83 | 0.56 | 0.83 | 0.94 |
| p14pcd | 0.96 | 0.97 | 0.42 | 0.95 | 0.78 | 0.91 | 0.63 | 0.92 | 0.83 | 0.93 | 0.94 | 0.91 | 0.75 | 0.87 | 0.59 | 0.85 | 0.95 |
| p14pu | 0.81 | 0.83 | 0.40 | 0.90 | 0.51 | 0.80 | 0.31 | 0.69 | 0.67 | 0.79 | 0.74 | 0.57 | 0.58 | 0.71 | 0.46 | 0.75 | 0.90 |
| p14pud | 0.88 | 0.88 | 0.46 | 0.94 | 0.69 | 0.83 | 0.45 | 0.92 | 0.67 | 0.79 | 0.75 | 0.59 | 0.61 | 0.72 | 0.52 | 0.90 | 0.94 |
| p15sc | 0.83 | 0.56 | 0.85 | 0.92 | 0.63 | 0.58 | 0.31 | 0.80 | 0.70 | 0.83 | 0.49 | 0.85 | 0.61 | 0.53 | 0.30 | 0.84 | 0.92 |
| p15scd | 0.88 | 0.62 | 0.88 | 0.90 | 0.69 | 0.63 | 0.18 | 0.85 | 0.72 | 0.86 | 0.54 | 0.88 | 0.66 | 0.58 | 0.15 | 0.84 | 0.90 |
| p21sc | 0.58 | 0.74 | 0.85 | 0.96 | 0.44 | 0.35 | 0.29 | 0.55 | 0.57 | 0.49 | 0.66 | 0.91 | 0.35 | 0.35 | 0.34 | 0.62 | 0.96 |
| p21scd | 0.86 | 0.86 | 0.52 | 0.76 | 0.65 | 0.79 | 0.47 | 0.74 | 0.58 | 0.50 | 0.68 | 0.92 | 0.36 | 0.55 | 0.34 | 0.62 | 0.77 |
| p21pc | 0.80 | 0.78 | 0.82 | 0.98 | 0.39 | 0.51 | 0.43 | 0.94 | 0.55 | 0.50 | 0.78 | 0.83 | 0.41 | 0.50 | 0.41 | 0.94 | 0.98 |
| p21pcd | 0.82 | 0.83 | 0.84 | 0.98 | 0.44 | 0.61 | 0.43 | 0.95 | 0.55 | 0.81 | 0.81 | 0.84 | 0.45 | 0.57 | 0.41 | 0.94 | 0.98 |
| p21pu | 0.81 | 0.86 | 0.89 | 0.99 | 0.44 | 0.68 | 0.23 | 0.98 | 0.65 | 0.79 | 0.82 | 0.87 | 0.43 | 0.67 | 0.27 | 0.97 | 0.99 |
| p21pud | 0.81 | 0.86 | 0.89 | 0.99 | 0.44 | 0.68 | 0.23 | 0.98 | 0.65 | 0.79 | 0.82 | 0.87 | 0.43 | 0.67 | 0.27 | 0.97 | 0.99 |
| p22sc | 0.50 | 0.60 | 0.53 | 0.96 | 0.43 | 0.27 | 0.40 | 0.95 | 0.70 | 0.48 | 0.55 | 0.60 | 0.48 | 0.30 | 0.42 | 0.95 | 0.96 |
| p22scd | 0.51 | 0.56 | 0.55 | 0.97 | 0.48 | 0.25 | 0.42 | 0.96 | 0.71 | 0.50 | 0.53 | 0.61 | 0.53 | 0.29 | 0.43 | 0.95 | 0.97 |
| p22pc | 0.42 | 0.33 | 0.47 | 0.81 | 0.34 | 0.24 | 0.32 | 0.80 | 0.74 | 0.53 | 0.41 | 0.62 | 0.40 | 0.03 | 0.37 | 0.97 | 0.81 |
| p22pcd | 0.59 | 0.46 | 0.40 | 0.82 | 0.36 | 0.24 | 0.30 | 0.81 | 0.76 | 0.58 | 0.48 | 0.62 | 0.42 | 0.05 | 0.35 | 0.97 | 0.82 |
| p22pu | 0.18 | 0.28 | 0.05 | 0.96 | 0.29 | 0.11 | -0.03 | 0.97 | 0.56 | 0.22 | 0.33 | 0.18 | 0.35 | 0.15 | 0.07 | 0.95 | 0.96 |
| p22pud | 0.66 | 0.16 | 0.31 | 0.96 | 0.30 | 0.08 | -0.02 | 0.97 | 0.73 | 0.26 | 0.36 | 0.21 | 0.40 | 0.14 | 0.07 | 0.96 | 0.96 |
| p23sc | 0.64 | 0.73 | 0.72 | 0.96 | 0.62 | 0.73 | 0.37 | 0.85 | 0.84 | 0.74 | 0.73 | 0.80 | 0.71 | 0.77 | 0.44 | 0.90 | 0.96 |
| p23scd | 0.64 | 0.72 | 0.72 | 0.96 | 0.62 | 0.72 | 0.36 | 0.86 | 0.84 | 0.73 | 0.72 | 0.50 | 0.71 | 0.76 | 0.44 | 0.90 | 0.96 |
| p24sc | 0.95 | 0.96 | 0.56 | 0.99 | 0.65 | 0.63 | 0.67 | 0.86 | 0.94 | 0.95 | 0.97 | 0.33 | 0.64 | 0.62 | 0.70 | 0.84 | 0.99 |
| p24scd | 0.97 | 0.97 | 0.63 | 0.99 | 0.64 | 0.63 | 0.68 | 0.99 | 0.95 | 0.97 | 0.98 | 0.61 | 0.63 | 0.63 | 0.71 | 0.98 | 0.99 |
| p24pc | 0.64 | 0.72 | 0.98 | 0.99 | 0.10 | 0.13 | 0.80 | 0.50 | 0.41 | 0.64 | 0.72 | 0.98 | 0.11 | 0.13 | 0.82 | 0.79 | 0.99 |
| p24pcd | 0.97 | 0.93 | 0.98 | 0.99 | 0.90 | 0.75 | 0.89 | 0.95 | 0.90 | 0.96 | 0.93 | 0.96 | 0.85 | 0.74 | 0.91 | 0.95 | 0.99 |
| p24pu | 0.05 | 0.08 | 0.17 | 0.16 | 0.08 | 0.06 | 0.08 | 0.13 | 0.03 | 0.23 | 0.23 | 0.18 | -0.02 | -0.02 | 0.05 | 0.87 | 0.16 |
| p24pud | 0.11 | 0.14 | 0.16 | 0.17 | 0.02 | 0.12 | 0.16 | 0.13 | 0.83 | 0.92 | 0.89 | 0.21 | 0.85 | 0.57 | 0.94 | 0.99 | 0.17 |
| p25sc | 0.96 | 0.95 | 0.92 | 0.96 | 0.73 | 0.41 | 0.88 | 0.97 | 0.90 | 0.98 | 0.91 | 0.98 | 0.78 | 0.47 | 0.89 | 0.95 | 0.96 |
| p25scd | 0.96 | 0.92 | 0.95 | 0.96 | 0.72 | 0.65 | 0.88 | 0.96 | 0.93 | 0.98 | 0.91 | 0.98 | 0.76 | 0.66 | 0.88 | 0.94 | 0.96 |
| p25pc | 0.93 | 0.94 | 0.88 | 0.97 | 0.78 | 0.82 | 0.77 | 0.96 | 0.87 | 0.95 | 0.95 | 0.92 | 0.79 | 0.84 | 0.80 | 0.97 | 0.97 |

TABLE 3-continued

Correlation Coefficients, r, Among Breath Waveforms from Respiratory Inductive Plethysmograph and Moving Time Average of Diaphragmatic Electromyogram During CO₂ Rebreathing: Flow Parameters (Nine Piglets)*

| | | | | | | | | | | | | | | | | | |
|---|---|---|---|---|---|---|---|---|---|---|---|---|---|---|---|---|---|
| p25pcd | 0.93 | 0.94 | 0.88 | 0.97 | 0.78 | 0.82 | 0.77 | 0.96 | 0.87 | 0.95 | 0.95 | 0.92 | 0.79 | 0.84 | 0.80 | 0.97 | 0.97 |
| p25pu  | 0.67 | 0.52 | 0.93 | 0.99 | 0.25 | 0.55 | 0.68 | 0.97 | 0.78 | 0.69 | 0.53 | 0.95 | 0.17 | 0.55 | 0.71 | 0.97 | 0.99 |
| p25pud | 0.89 | 0.82 | 0.56 | 0.97 | 0.73 | 0.58 | 0.82 | 0.96 | 0.92 | 0.91 | 0.83 | 0.89 | 0.77 | 0.62 | 0.86 | 0.97 | 0.97 |
| Mean** | .70  | .67  | .58  | .81  | .53  | .55  | .44  | .79  | .75  | .76  | .71  | .75  | .62  | .55  | .55  | .89  | .82  |
| SD**   | .37  | .36  | .37  | .34  | .31  | .32  | .35  | .35  | .15  | .21  | .25  | .23  | .18  | .29  | .26  | .10  | .34  |

*Legend: sc = calibrated with QDC in supine posture; pu = prone posture with calibration from sc; pc = calibrated with QDC in prone posture; d after sc, pu or Pc indicates that trials in which outlier data values were deleted; No. Breaths Analyzed = number breaths analyzed; No. Breaths Deleted = number breaths deleted because they were outliers; Ventil = ventilation breath by breath; RIP respiratory inductive plethysmograph; Edi = moving time average diaphragmatic; electromyogram; EdiA = amplitude Edi; TI = inspiratory time; Edi/TI = mean slope Edi; PIF Vt = peak inspiratory flow tidal volume (Vt RIP); PIF RC = peak inspiratory flow (RC RIP); PIF AB = peak inspiratory flow AB; EdiPS = peak slope Edi; Vt/TI = mean inspiratory flow Vt (RIP); RC/TI = mean inspiratory flow RC (RIP); AB/TI - mean inspiratory flow AB (RIP)

TABLE 4

Correlation Coefficients, r, Among Breath Waveforms from Respiratory Inductive Plethysmograph and Moving Time Average of Diaphragmatic Electromyogram During $CO_2$ Rebreathing: Acceleration Parameters (Nine Piglets)*

| | No. Breaths Analyzed | No. Breaths Deleted | r(PIA Vt vs Ventil) | r(PIA RC vs Ventil) | r(PIA AB vs Ventil) | r(PIA Edi vs Ventil) | r(PIA Vt vs EdiA/Ti) | r(PIA RC vs EdiA/Ti) | r(PIA AB vs EdiA/Ti) | r(PIA vs EdiA vs EdiA/Ti) | r(PIA Vt vs EdiA) |
|---|---|---|---|---|---|---|---|---|---|---|---|
| p11scd | 168 | 20 | 0.77 | 0.65 | 0.34 | 0.64 | 0.48 | 0.42 | 0.16 | 0.33 | −0.43 |
| p11pcd | 187 | 16 | 0.71 | −0.04 | 0.30 | 0.57 | 0.13 | 0.16 | 0.15 | 0.12 | −0.11 |
| p13scd | 333 | 15 | 0.96 | 0.97 | 0.77 | 0.86 | 0.71 | 0.73 | 0.61 | 0.67 | 0.68 |
| p13pud | 244 | 25 | 0.84 | 0.85 | 0.30 | 0.80 | 0.49 | 0.48 | 0.16 | 0.58 | 0.46 |
| p14scd | 227 | 25 | 0.80 | 0.92 | 0.04 | 0.87 | 0.45 | 0.45 | 0.04 | 0.48 | 0.42 |
| p14pud | 211 | 22 | 0.77 | 0.90 | 0.72 | 0.85 | 0.42 | 0.46 | 0.27 | 0.47 | 0.39 |
| p14pcd | 245 | 15 | 0.67 | 0.81 | 0.66 | 0.83 | 0.57 | 0.67 | 0.32 | 0.74 | 0.56 |
| p15scd | 192 | 40 | 0.65 | 0.93 | 0.59 | 0.83 | 0.51 | 0.82 | 0.53 | 0.83 | 0.39 |
| p21scd | 174 | 8 | 0.90 | 0.90 | 0.21 | 0.47 | 0.42 | 0.41 | −0.04 | 0.12 | 0.50 |
| p21pud | 173 | 5 | 0.93 | 0.86 | 0.55 | 0.78 | 0.91 | 0.79 | 0.45 | 0.74 | 0.74 |
| p21pcd | 200 | 20 | 0.94 | 0.92 | 0.86 | 0.89 | 0.89 | 0.87 | 0.77 | 0.90 | 0.79 |
| p22scd | 133 | 13 | 0.86 | 0.78 | 0.69 | 0.84 | 0.78 | 0.64 | 0.65 | 0.84 | 0.53 |
| p23scd | 105 | 5 | 0.72 | 0.70 | 0.48 | 0.72 | 0.69 | 0.67 | 0.41 | 0.66 | 0.44 |
| p24scd | 149 | 9 | 0.34 | 0.57 | 0.19 | 0.39 | 0.39 | 0.60 | 0.23 | 0.41 | 0.36 |
| p24pud | 125 | 16 | 0.41 | 0.59 | 0.23 | 0.33 | 0.27 | 0.69 | 0.03 | 0.12 | 0.25 |
| p24pcd | 136 | 15 | 0.19 | 0.25 | 0.23 | 0.26 | −0.01 | 0.08 | 0 | 0.04 | 0.09 |
| p25scd | 182 | 21 | 0.84 | 0.50 | 0.57 | 0.70 | 0.82 | 0.45 | 0.52 | 0.74 | 0.73 |
| p25pud | 168 | 19 | 0.90 | 0.56 | 0.84 | 0.88 | 0.85 | 0.50 | 0.76 | 0.92 | 0.78 |
| p25pcd | 218 | 27 | 0.94 | 0.80 | 0.74 | 0.88 | 0.91 | 0.74 | 0.74 | 0.95 | 0.86 |
| MEAN** | 188 | 18 | 0.74 | 0.71 | 0.49 | 0.70 | 0.56 | 0.56 | 0.36 | 0.56 | 0.44 |
| SD** | 53 | 8 | 0.22 | 0.26 | 0.25 | 0.20 | 0.27 | 0.21 | 0.27 | 0.3 | 0.32 |

| | r(PIA RC vs EdiA) | r(PIA AB vs EdiA) | r(PIA Edi vs EdiA) | r(PIA Vt vs EdiPS) | r(PIA RC vs EdiPS) | r(PIA AB vs EdiPS) | r(PIA Edi vs EdiPS) | r(PIA Vt vs PIF Vt) | r(PIA RC vs PIF Vt) | r(PIA AB vs PIF Vt) | r(PIA Edi vs PIF Vt) |
|---|---|---|---|---|---|---|---|---|---|---|---|
| p11scd | −0.28 | 0.12 | −0.42 | 0.20 | 0.18 | 0.02 | 0.12 | 0.86 | 0.73 | 0.37 | 0.63 |
| p11pcd | 0.24 | 0.04 | −0.07 | −0.06 | 0.15 | 0.06 | 0 | 0.92 | 0.02 | 0.34 | 0.65 |
| p13scd | 0.70 | 0.59 | 0.63 | 0.60 | 0.62 | 0.52 | 0.58 | 0.97 | 0.97 | 0.79 | 0.86 |
| p13pud | 0.47 | 0.08 | 0.60 | 0.35 | 0.34 | 0.14 | 0.48 | 0.75 | 0.75 | 0.29 | 0.65 |
| p14scd | 0.46 | −0.05 | 0.54 | 0.64 | 0.67 | 0.12 | 0.72 | 0.13 | 0.36 | −0.48 | 0.40 |
| p14pud | 0.43 | 0.27 | 0.44 | −0.15 | −0.15 | −0.10 | −0.23 | 0.84 | 0.94 | 0.65 | 0.90 |
| p14pcd | 0.68 | 0.37 | 0.76 | 0.55 | 0.65 | 0.36 | 0.68 | 0.77 | 0.87 | 0.58 | 0.87 |
| p15scd | 0.82 | 0.48 | 0.79 | 0.51 | 0.81 | 0.52 | 0.84 | 0.77 | 0.94 | 0.62 | 0.84 |
| p21scd | 0.49 | −0.13 | 0.17 | 0.40 | 0.40 | −0.11 | 0.18 | 0.96 | 0.95 | 0.20 | 0.50 |
| p21pud | 0.72 | 0.34 | 0.65 | 0.74 | 0.72 | 0.39 | 0.75 | 0.94 | 0.90 | 0.51 | 0.74 |
| p21pcd | 0.79 | 0.71 | 0.85 | 0.79 | 0.79 | 0.69 | 0.96 | 0.95 | 0.95 | 0.83 | 0.89 |
| p22scd | 0.45 | 0.43 | 0.63 | 0.48 | 0.42 | 0.37 | 0.62 | 0.95 | 0.82 | 0.77 | 0.90 |
| p23scd | 0.50 | 0.33 | 0.67 | 0.52 | 0.56 | 0.45 | 0.77 | 0.78 | 0.67 | 0.66 | 0.69 |
| p24scd | 0.60 | 0.20 | 0.33 | 0.31 | 0.61 | 0.13 | 0.23 | 0.34 | 0.57 | 0.20 | 0.41 |
| p24pud | 0.66 | −0.03 | 0.09 | 0.24 | 0.68 | −0.01 | 0.09 | 0.25 | 0.55 | −0.05 | 0.10 |
| p24pcd | 0.21 | 0.12 | 0.18 | 0.04 | 0.21 | 0.06 | 0.14 | 0.08 | 0.20 | 0.08 | 0.13 |
| p25scd | 0.37 | 0.49 | 0.67 | 0.78 | 0.42 | 0.52 | 0.67 | 0.89 | 0.43 | 0.57 | 0.40 |
| p25pud | 0.51 | 0.70 | 0.90 | 0.81 | 0.48 | 0.73 | 0.92 | 0.91 | 0.57 | 0.87 | 0.89 |
| p25pcd | 0.70 | 0.70 | 0.92 | 0.87 | 0.72 | 0.71 | 0.95 | 0.96 | 0.82 | 0.74 | 0.90 |
| MEAN** | 0.50 | 0.30 | 0.49 | 0.45 | 0.49 | 0.29 | 0.50 | 0.74 | 0.68 | 0.45 | 0.65 |
| SD** | 0.25 | 0.26 | 0.36 | 0.30 | 0.25 | 0.28 | 0.36 | 0.30 | 0.28 | 0.35 | 0.26 |

*Legend: sc = calibrated with QDC in supine posture; pu = prone posture with calibration from sc; pc = calibrated with QDC in prone posture; d after sc, pu or pc indicates that trials in which outlier data values were deleted; No. Breaths Analyzed = number breaths analyzed; No. Breaths Deleted = number breaths deleted because they were outliers; Ventil = ventilation breath by breath; RIP respiratory inductive plethysmograph; Edi = moving time average diaphragmatic electromyogram; EdiA = amplitude Edi; Ti = inspiratory time; EdiA/Ti = mean slope Edi; PIF Vt = peak inspiratory flow tidal volume (Vt RIP); PIA Vt = peak inspiratory acceleration Vt RIP; PIA RC = peak inspiratory acceleration RC (RC RIP); PIA AB = peak inspiratory acceleration AB (AB RIP); EdiPS = peak slope Edi;
**Means and SD from trials in which outlier data values were deleted

TABLE 5

Ranked Correlation Coefficients, r, Among Breath Waveforms from Respiratory Inductive Plethysmograph and Moving Time Average of Diaphragmatic Electromyogram During $CO_2$ Rebreathing: Flow and Acceleration Parameters (Nine Piglets)

| Flow Variables RIP | Mean correlation coefficents r | Acceleration Variables RIP | Mean correlation coefficents r |
|---|---|---|---|
| PIF Vt vs EdiA/Ti | 0.80 | PIA Vt vs EdiA/Ti | 0.56 |
| PIF Vt vs EdiPS | 0.76 | PIA RC vs EdiA/Ti | 0.56 |
| PIF AB vs EdiPS | 0.75 | PIA RC vs EdiA | 0.50 |
| PIF RC vs EdiA/Ti | 0.73 | PIA RC vs EdiPS | 0.49 |
| PIF AB vs EdiA/Ti | 0.72 | PIA Vt vs EdiPS | 0.45 |
| PIF RC vs EdiPS | 0.71 | PIA Vt vs EdiA | 0.44 |
| Vi/Ti vs EdiA/Ti | 0.70 | PIA AB vs EdiA/Ti | 0.36 |
| PIF Vt vs EdiA | 0.70 | PIA AB vs EdiA | 0.30 |
| PIF RC vs EdiA | 0.67 | PIA AB vs EdiPS | 0.29 |
| Vt/Ti vs EdiPS | 0.62 | | |
| RC/Ti vs EdiA/Ti | 0.60 | | |
| AB/Ti vs Edia/Ti | 0.59 | | |
| PIF AB vs EdiA | 0.58 | | |
| RC/Ti vs EdiA | 0.55 | | |
| RC/Ti vs EdiPS | 0.55 | | |
| AB/Ti vs EdiPS | 0.55 | | |
| Vt/Ti vs EdiA | 0.53 | | |
| AB/Ti vs EdiA | 0.44 | | |

*Legend RIP = respiratory inductive plethysmograph; PIF Vt = peak inspiratory flow tidal volume (Vt RIP); PIF RC = peak inspiratory flow RC (RC RIP); PIF AB = peak inspiratory flow AB (AB RIP); Vt/Ti = mean inspiratory flow (Vt RIP); RC/Ti = mean inspiratory flow RC (RC RIP); AB/Ti = mean inspiratory flow AB (AB RIP); Edi = movingtime average diaphragmatic electromyogram; EdiA = amplitude Edi; Ti = inspiratory time; EdiA/Ti = mean slope Edi; EdiPS = peak slope Edi; PIA Vt = peak inspiratory acceleration Vt RIP; PIA RC = peak inspiratory acceleration RC (RC RIP); PIA AB = peak inspiratory acceleration AB (AB RIP)

TABLE 6

Ranked Correlation Coefficients, r, Among Breath Waveforms from Respiratory Inductive Plethysmograph and Moving Time Average of Diaphragmatic Electromyogram During $CO_2$ Rebreathing: Plotted Against Ventilation (Nine piglets)*

| Ventilation | r |
|---|---|
| PIF Vt | 0.85 |
| EdiA/Ti | 0.82 |
| Vt/Ti | 0.78 |
| EdiPS | 0.75 |
| PIF RC | 0.75 |
| PIA Vt | 0.74 |
| PIF AB | 0.74 |
| RC/Ti | 0.70 |
| PIA RC | 0.69 |
| EdiA | 0.67 |
| PIA Edi | 0.67 |
| AB/Ti | 0.60 |
| PIA AB | 0.49 |

*Legend PIF Vt = peak inspiratory flow tidal volume (Vt RIP); PIF RC = peak inspiratory flow RC (RC RIP); PIF AB = peak inspiratory flow AB (AB RIP); Vt/Ti = mean inspiratory flow (Vt RIP); RC/Ti = mean inspiratory flow RC (RC RIP); AB/Ti = mean inspiratory flow AB (AB RIP); Edi = moving time average diaphragmatic electromyogram; EdiA = amplitude Edi;Ti = inspiratory time; EdiA/Ti = mean slope Edi; EdiPS = peak slope Edi; PIA Vt = peak inspiratory accelaration Vt RIP; PIA RC = peak inspiratory acceleration RC (RC RIP); PIA AB = peak inspiratory acceleration AB (AB RIP)

TABLE 7

Respiratory and Diaphragmatic Electromyographic Parameters of Respiratory Drive during Manual Occlusion of Airway in Piglets

| State | EdiA | PIF AB | EdiA/Ti | PIA AB | PIA Edi |
|---|---|---|---|---|---|
| Baseline | 39 | 70 | 146 | 75 | 151 |
| Occlusion | 68 | 51 | 133 | 85 | 144 |
| P | <.02 | n.s. | n.s. | n.s. | n.s. |

Legend. EdiA = amplitude of mtaEdi; PIF AB = peak inspiratory flow of AB; EdiA/Ti = mean slope of moving time average diaphragmatic electomyogram; PIA AB = peak inspiratory acceleration; PIA Edi = peak inspiratory accelerafion of mtaEdi

TABLE 8

| R | Ptp cm $H_2O$ | | PNT Ventilation l/m | | PIF AB | | PIF PNT | | PIF AB/ Ventilation | | PIA AB | |
|---|---|---|---|---|---|---|---|---|---|---|---|---|
| | I | E | I | E | I | E | I | E | I | E | I | E |
| 0 | 1.0 | 1.5 | 1.8 | 2.1 | 118 | 139 | 100 | 115 | 3.8 | 3.8 | 178 | 122 |
| 50 | 3.6 | 3.8* | 1.7 | 2.1 | 110 | 141 | 88 | 124 | 3.6 | 4.0 | 122 | 165 |
| 200 | 12* | 8* | 1.7 | 1.6 | 119 | 141 | 114 | 136 | 4.2 | 5.4 | 146 | 143 |
| 500 | 23* | 10* | 2.1 | 1.3* | 155 | 163 | 220* | 152 | 4.9* | 7.7* | 245* | 169 |
| 1000 | 30* | 13* | 2.3 | 1.2* | 167 | 201* | 297* | 182 | 5.7* | 11.0* | 293* | 241 |
| R I + E [250 = 200 I + 50 E, 1500 = 1000 I + 500 E] | | | | | | | | | | | | |
| 0 | 1.1 | | 1.9 | | 110 | | 102 | | 3.4 | | 126 | |
| 250 | 15* | | 1.6 | | 128 | | 145 | | 4.8 | | 270 | |
| 1500 | 43* | | 4.1* | | 320* | | 591* | | 7.5* | | 526* | |

TABLE 9

| Parameters | Saline M (SD) | Carbachol M (SD) | P |
|---|---|---|---|
| Rate (breath/m) | 13.9 (5.6) | 17.4 (7.3) | <0.01 |
| Vt/Ti (ml/s) | 136 (40) | 161 (57) | <0.05 |
| PIA Vt (Ml/s$^2$) | 175 (81) | 279 (136) | <0.05 |
| PIA Vt Pneumotachograph (ml/s$^2$) | 119 (55) | 177 (76) | <0.05 |

We claim:

1. A method for measuring respiratory drive of a living subject, comprising the steps of:
   monitoring a breath waveform of the subject;
   determining from the monitored breath waveform one of a peak inspiratory flow and a peak inspiratory acceleration of the subject;
   determining the respiratory drive of the subject from said determined one of the peak inspiratory flow and peak inspiratory acceleration.

2. The method of claim 1, wherein said step of monitoring a breath waveform comprises the steps of measuring a rib cage motion and an abdominal motion of the subject, and determining a tidal volume from a sum of the rib cage motion and the abdominal motion, and wherein said step of determining one of the peak inspiratory flow and the peak inspiratory acceleration comprises determining said one of the peak inspiratory flow and the peak inspiratory acceleration at a predetermined time selected in response to one of the measured rib cage motion, the measured abdominal motion, and the determined tidal volume.

3. The method of claim 1, wherein said step of monitoring a breath waveform comprises measuring one of tidal flow and airflow of the subject.

4. The method of claim 1, wherein said step of monitoring a breath waveform comprises using one of a spirometer, a pneumatograph, a body plethysmograph, naso-oral thermistor, and a naso-oral thermocouple to monitor the breath waveform of the subject.

5. The method of claim 1, wherein said step of monitoring a breath waveform comprises measuring respiration of the subject using an instrument that is applied externally to a body surface of the subject.

6. The method of claim 1, wherein staid step of monitoring a breath waveformn comprises using one of a respiratory inductive plethysmograph, a jerkin plethysmograph, a linear differential transformer, a magnetometer, a bellows pneumograph, a strain gauge, a piezoelectric device, an inductance circumferential transformer, an impedance pneumograph, and a video transformation of torso movements to monitor the breath waveform of the subject.

7. The method of claim 1, wherein said step of determining one of peak inspiratory flow and peak inspiratory acceleration of the subject comprises determining the peak inspiratory acceleration using one of airway pressure, intrapleural pressure, transdiaphragmatic pressure, neck inductive plethysmography, and breath sound measurements.

8. The method of claim 1, wherein said step of determining one of peak inspiratory flow and peak inspiratory acceleration of the subject comprises determining the peak inspiratory acceleration within a window of ±300 msec. from a beginning of subject inspiration.

9. The method of claim 1, wherein said step of determining one of peak inspiratory flow and peak inspiratory acceleration of the subject comprises determining said one of peak inspiratory flow and peak inspiratory acceleration on one of a breath by breath and a time average basis.

10. The method of claim 1, further comprising the step of using the determined respiratory drive for one of assessing integrity of a respiratory center in the brain of the subject by breathing of one of $CO_2$ and low $O_2$ gas mixtures, assessing baseline respiratory center activity of the subject across wake and sleep states of the subject, assessing respiratory center drive of the subject during obstructive apneas/hypopneas, detecting presence of external expiratory resistive loading in the subject during sleep, providing a set-point for titration of positive airway pressure of the subject where the subject one of snores and has upper airway resistance syndrome, monitoring for presence of bronchoconstriction in the subject, gauging an effect in the subject of anesthetic, sedative and analgesic agents that usually depress respiratory drive, categorizing respiratory drive in the subject as a measure of status of a disease in the subject, assessing status of respiratory drive turing mechanical ventilation of the subject, assessing status of respiratory muscles of the subject during potentially fatiguing tasks undertaken by the subject, indirectly signaling hypoxemic events in newborn subjects, signaling retained tracheobronchial secretions in the subject, diagnosing nocturnal brochospasm in the subject during sleep, detecting respiratory center depression in the subject after administration of narcotics to the subject to depress excessively high respiratory drive, monitoring for presence of intrinsic positive end expiratory pressure (PEEP) in the subject, and detecting respiratory distress in subjects working in hazardous gaseous environments.

11. The method of claim 2, further comprising the steps of generating a trigger pulse signal when one of the tidal volume, inspiratory flow, and inspiratory acceleration exceeds a threshold value.

12. The method of claim 11, wherein said step of generating a trigger pulse comprises using one of the tidal volume, inspiratory flow, and inspiratory acceleration derived from a leading one of the rib cage motion and the abdominal motion.

13. The method of claim 12, further comprising the step of selecting the leading one of the rib cage motion and the abdominal motion using one of manual selection and automatic selection.

14. The method of claim 11, further comprising the step of transmitting the trigger pulse signal to a mechanical ventilator connected to the subject for initiating inflation by the mechanical ventilator in response to the trigger pulse.

15. The method of claim 2, further comprising the steps of determining ventilation from the product of respiratory rate and tidal volume, and calculated a ratio of the peak inspiratory acceleration to the ventilation as a measure of breathlessness.

16. The method of claim 15, further comprising the step of determining an optimal pressure level for a continuous positive air pressure (CPAP) device connected to the subject in response to one of the respiratory drive and a ratio of the respiratory drive to the ventilation.

17. The method of claim 16, wherein step of determining an optimal pressure level comprises determining an optimal pressure level of a CPAP device connected to the subject where the subject has one of obstructive sleep apnea, hypoapnea, upper airway resistance syndrome, and dynamic hyperinflation.

18. The method of claim 1, wherein said step of monitoring a breath waveform comprises using a respiratory inductive plethysograph to monitor the breath waveform, and wherein said method further comprises the steps of measuring a mean inspiratory flow from the breath waveform, and controlling a pressure level of a continuous positive air pressure (CPAP) device connected to the subject in response to a value computed by dividing the peak inspiratory flow by the mean inspiratory flow.

19. The method of claim 1, wherein said step of monitoring a breath waveform comprises using a respiratory inductive plethysograph to monitor the breath waveform, and wherein said method further comprises the steps of measuring a mean expiratory flow and a peak expiratory flow from the breath waveform, and controlling a pressure level of a continuous positive air pressure (CPAP) device connected to the subject in response to a value computed by dividing the peak expiratory flow by the mean expiratory flow.

20. A method for measuring a respiratory drive of a subject, comprising the steps of:

measuring a rib cage motion and an abdominal motion of the subject;

determining a tidal volume of a respiratory system of the subject from a sum of the measured rib cage motion and the measured abdominal motion;

determining one of a peak inspiratory flow and a peak inspiratory acceleration of the subject from one of the rib cage motion, the abdominal motion and the tidal volume; and determining the respiratory drive from said one of the peak inspiratory flow and the peak inspiratory acceleration.

21. The method of claim 20, wherein said step of measuring a rib cage motion and an abdominal motion comprises using an instrument that is applied externally to a body surface of the patient subject to measure said motion.

22. The method of claim 20, wherein said step of measuring a rib cage motion and an abdominal motion comprises using one of a respiratory inductive plethysmograph, jerkin plethysmograph, linear differential transformer, magnetometer, bellows pneumograph, strain gauges, piezoelectric devices, inductance circumferential transformers, impedance pneumograph, and video transformation of torso movements.

23. The method of claim 20, wherein said step of determining one of peak inspiratory flow and peak inspiratory acceleration of the subject comprises determining the peak inspirator acceleration within a window of ±300 msec. from a beginning of inspiration of the subject.

24. The method of claim 20, wherein said step of determining one of peak inspiratory flow and peak inspiratory acceleration of the subject comprises determining said one of peak inspiratory flow and peak inspiratory acceleration on one of a breath by breath and a time average basis.

25. The method of claim 20, further comprising the steps of measuring an inspiratory flow and an inspiratory acceleration of the subject, and generating a trigger pulse signal when one of the tidal volume, inspiratory flow, and inspiratory acceleration exceeds a threshold value.

26. The method of claim 25, wherein said step of generating a trigger pulse comprises using one of the tidal volume, inspiratory flow, and inspiratory acceleration derived from a leading one of the rib cage motion and the abdominal motion.

27. The method of claim 26, further comprising the step of selecting the leading one of the rib cage motion and the abdominal motion using one of manual selection and automatic selection.

28. The method of claim 25, further comprising the step of transmitting the trigger pulse signal to a mechanical ventilator connected to the subject for initiating inflation by the mechanical ventilator in response to the trigger pulse.

29. The method of claim 20, further comprising the steps of measuring the respiratory rate of the subject, determining ventilation of the subject from the product of respiratory rate and the tidal volume, and calculating a ratio of the peak inspiratory acceleration to the ventilation as a measure of breathlessness.

30. The method of claim 29, further comprising the step of determining an optimal pressure level for a continuous positive air pressure (CPAP) device connected to the subject in response to one of the respiratory drive and a ratio of the respiratory drive to the ventilation.

31. The method of claim 30, wherein said step of determining an optimal pressure level comprises determining an optimal pressure level of a CPAP device connected to the subject where the subject has one of obstructive sleep apnea, hypoapnea, upper airway resistance syndrome, and dynamic hyperinflation.

32. The method of claim 20, further comprising the steps of measuring a mean inspiratory flow in the subject, and controlling a pressure level of a continuous positive air pressure (CPAP) device connected to the subject in response to a value computed by dividing the peak inspiratory flow by the mean inspiratory flow.

33. The method of claim 20, further comprising the steps of measuring a mean expiratory flow and a peak expiratory flow of the subject, and controlling a pressure level of a continuous positive air pressure (CPAP) device connected to the subject in response to a value computed by dividing the peak expiratory flow by the mean expiratory flow.

34. The method of claim 20, wherein said step of measuring rib cage motion and abdominal motion of the subject comprises using a respiratory inductive plethysmograph connected to the subject and wherein said method further comprises the steps of determining an index that describes a shape of inspiratory and expiratory waveforms derived from the measured rib cage motion and the measured abdominal motion, and controlling a continuous positive air pressure (CPAP) device connected to the subject using a damped closed loop control system in response to the determined index.

35. The method of claim 20, wherein said step of measuring rib cage motion and abdominal motion of the subject comprises using a plethysmograph device connected to the subject and having a sample rate of at least about 200 points per second or greater.

36. The method of claim 20, wherein said step of measuring rib cage motion and abdominal motion of the subject comprises using a plethysmograph device connected to the subject and having an oscillator located directly on a transducer band of the device for reducing crosstalk and thereby accommodating a quantity of oscillator generated signals.

37. The method of claim 25, wherein said step of measuring an inspiration flow and an inspiratory acceleration of the subject comprises using a plethysmograph device connected to the subject and having a sample rate of at least about 200 points per second or greater.

* * * * *